(12) United States Patent
Ben-Yakar et al.

(10) Patent No.: US 7,834,331 B2
(45) Date of Patent: Nov. 16, 2010

(54) PLASMONIC LASER NANOABLATION METHODS

(75) Inventors: Adela Ben-Yakar, Austin, TX (US); Daniel Eversole, Austin, TX (US); Xun Guo, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 236 days.

(21) Appl. No.: 12/184,628

(22) Filed: Aug. 1, 2008

(65) Prior Publication Data

US 2009/0072161 A1    Mar. 19, 2009

Related U.S. Application Data

(60) Provisional application No. 60/953,316, filed on Aug. 1, 2007, provisional application No. 60/971,377, filed on Sep. 11, 2007.

(51) Int. Cl.
*A61N 5/00* (2006.01)
*A61F 7/12* (2006.01)

(52) U.S. Cl. .................. 250/492.1; 607/89; 607/99; 607/100; 604/19; 604/20; 606/2; 606/33; 606/34; 428/913

(58) Field of Classification Search .......... 250/492.1; 607/88, 89, 92, 99, 100, 105; 604/19, 20; 606/2, 10, 14, 15, 16, 33; 428/913
See application file for complete search history.

(56) References Cited

U.S. PATENT DOCUMENTS 6,344,272 B1    2/2002    Oldenburg et al.
6,530,944 B2    3/2003    West et al.
2003/0193982 A1*    10/2003    Farahi et al. .............. 372/75
2008/0241262 A1*    10/2008    Lee et al. .............. 424/490

OTHER PUBLICATIONS

Liu et al., "Measuring plasmon-resonance enhanced third harmonic (3) of Ag nanoparticles", Appl. Phys. Lett. 89, 041322, 2006.*
Huang et al., "Determination of the Minimum Temperature Required for Selective Photothermal Destruction of Cancer Cells with the Use of Immunotargeted Gold Nanoparticles", Photochemistry and Photobiology 2006 (82) 412-417.*

(Continued)

*Primary Examiner*—Bernard E Souw
(74) *Attorney, Agent, or Firm*—Baker Botts L.L.P.

(57) ABSTRACT

A novel femtosecond laser nano-ablation technique called Plasmonic Laser Nano-Ablation (PLN). The technique takes advantage of surface-enhanced plasmonic scattering of ultrashort laser pulses by nanoparticles to vaporize sub-cellular structures in attoliter volumes. The use of nanoparticles may overcome problems associated with current FLMS techniques and does not rely on heating for nanodisruption. In PLN, the particle acts as a "nano-lens," restricting laser light to the near-field of the particle, and only photodisrupting structures that are nanometers away. This eliminates the need for a tightly focused beam, while still achieving nanoscale ablation resolution. Moreover, the enhanced scattering around the particles reduces the amount of required laser fluence. A method is provided comprising positioning a nanoparticle in proximity to a surface of a material; irradiating the nanoparticle with a laser tuned close to the nanoparticle's plasmonic frequency; and allowing a near-field effect from the irradiated nanoparticle to photodamage the material.

20 Claims, 33 Drawing Sheets

OTHER PUBLICATIONS

Adela Ben-Yakar, "NER: Nanoparricle-Assisted Plasmonic Laser Surgery", NSF Award # 0508266, Jun. 3, 2005.*

M. Quinten, "Local Fields close to the surface of nanoparticles and aggregrates of particles." Appl. Phys. B 73, 2001, pp. 245-255.

Plech, et al., "Femtosecond laser near-field ablation from gold particles." Nature Physics 2, 2006, pp. 44-47.

Messinger, et al., "Local fields at the surface of noble-metals microspheres." Phys Rev B 24(2), 1981, pp. 649-657.

Kelly, et al., "The optical properties of metal nanoparticles: the influence of size, shape, and dielectric environment." J. Phys. Chem. B 107, 2003, pp. 668-677.

Huttmann, et al., "High precision cell surgery with nanoparticles?" Med. Laser Appl. 17, 2002, pp. 9-14.

Huttmann, et al., "Model system for investigating laser-induced subcellular microeffects." Proc. SPIE, 2001, vol. 4257, pp. 398-409.

Pitsillides, et al., "Selective cell targeting with light-absorbing microparticles and nanoparticles." Biophys. J. 84, 2003, pp. 4023-4032.

Yanik, et al., "Functional regeneration after laser axotomy." Nature 432, 2004, p. 882.

O'Neal, et al., "Photo-thermal tumor ablation in mice using near infrared-absorbing nanoparticles." Cancer Lett., 2004.

* cited by examiner

Figure 1
(a) Femtosecond laser micro-surgery
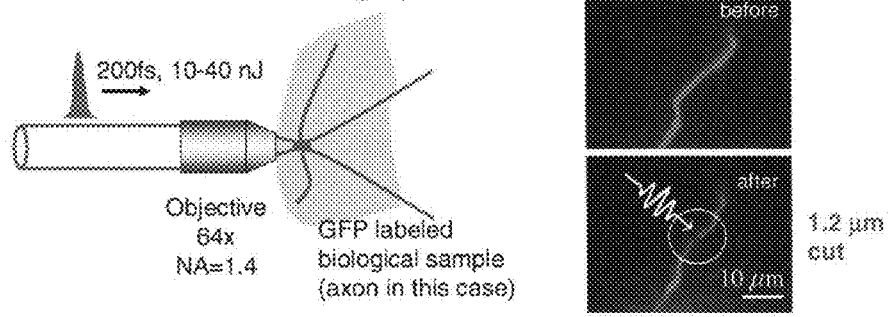
(b) Plasmonic laser nano-surgery
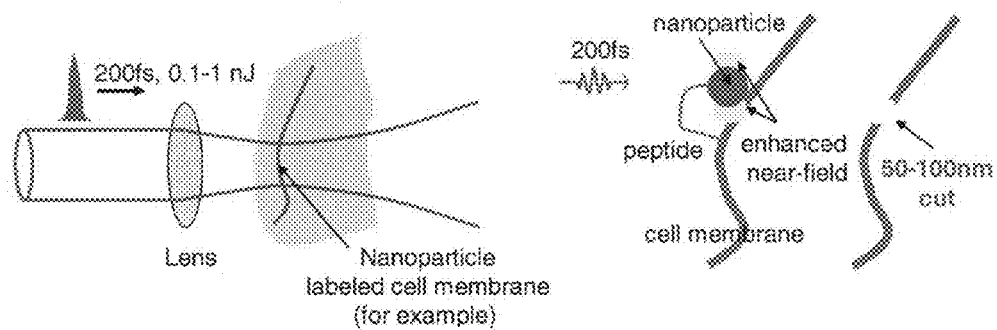

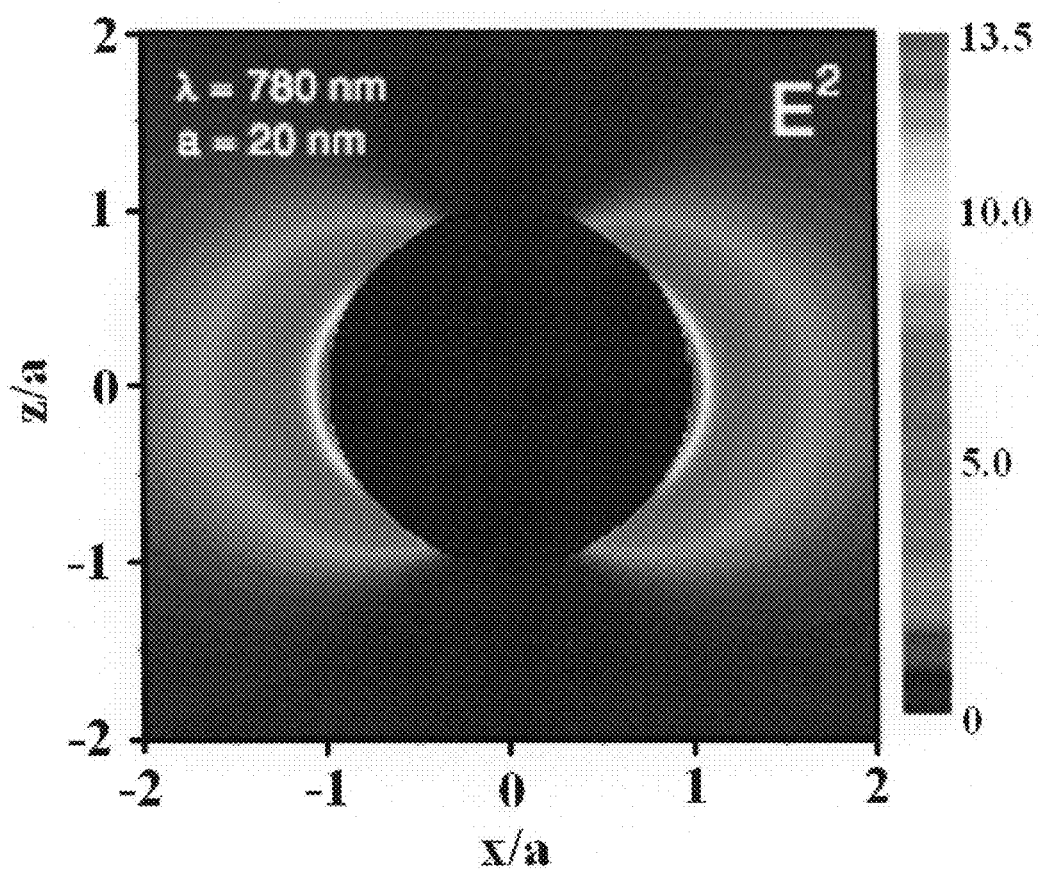

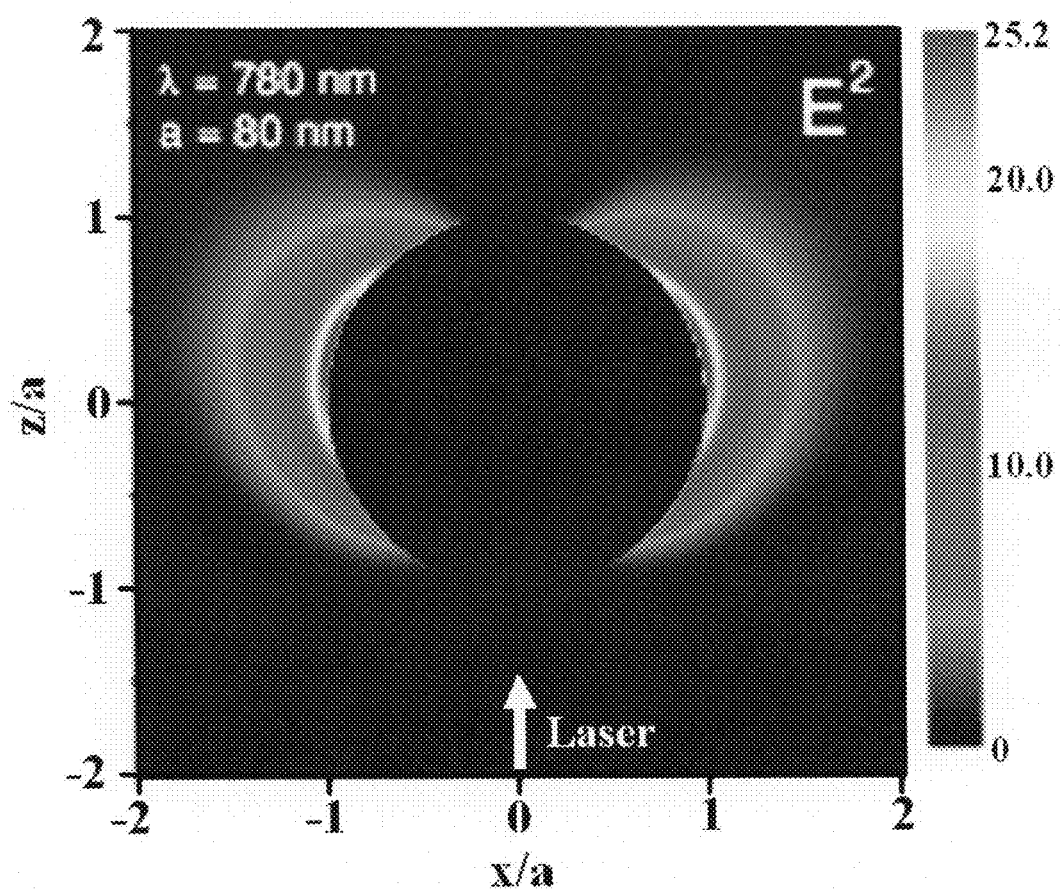

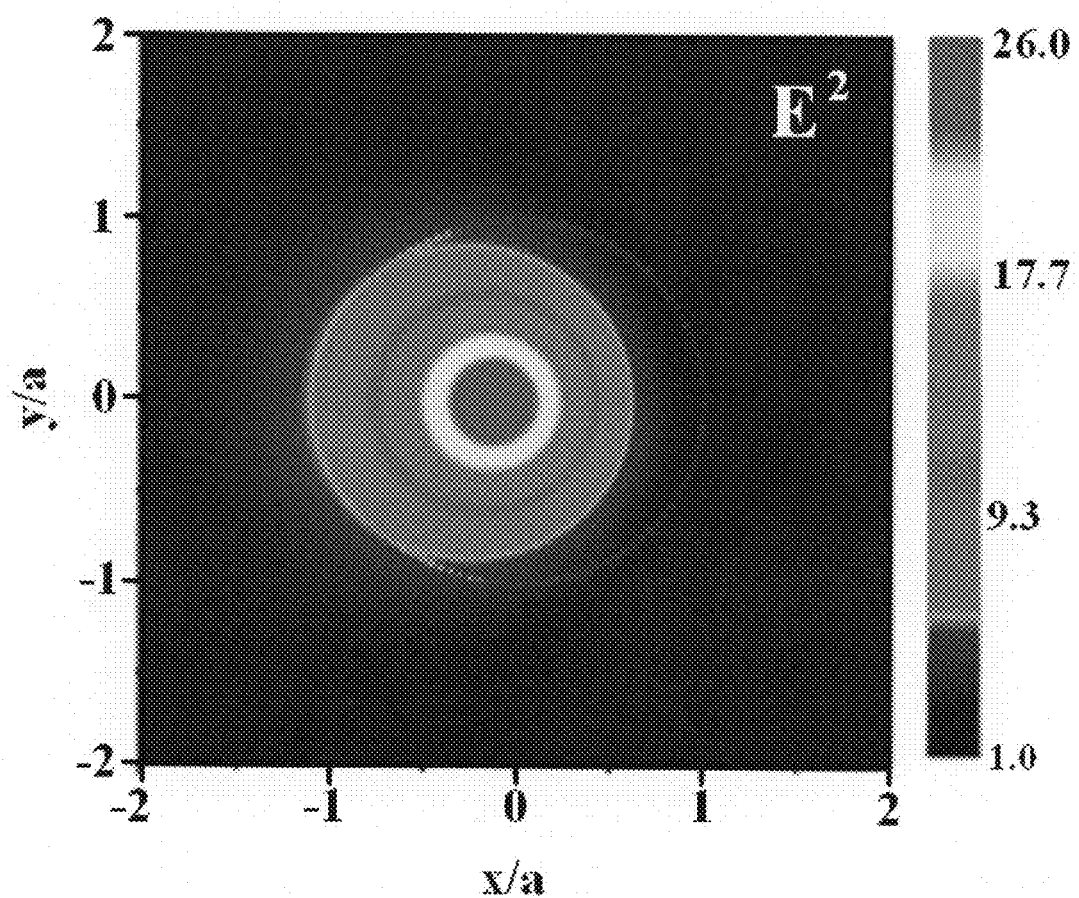

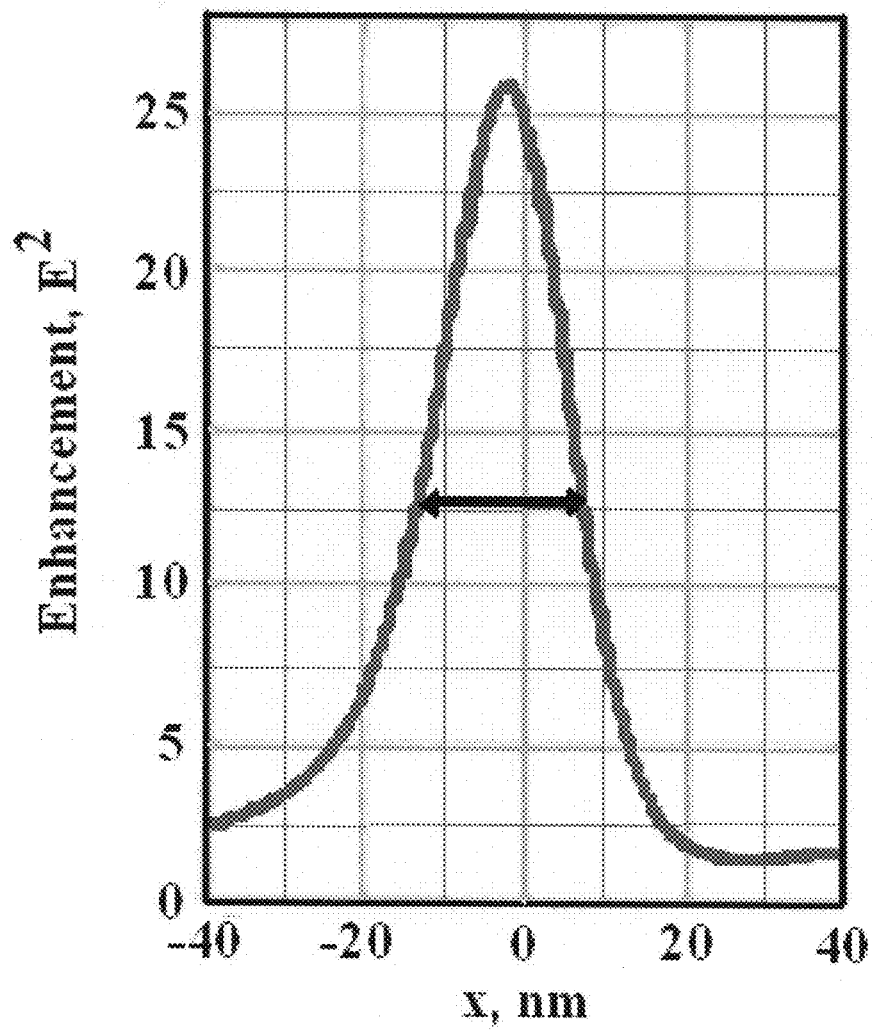

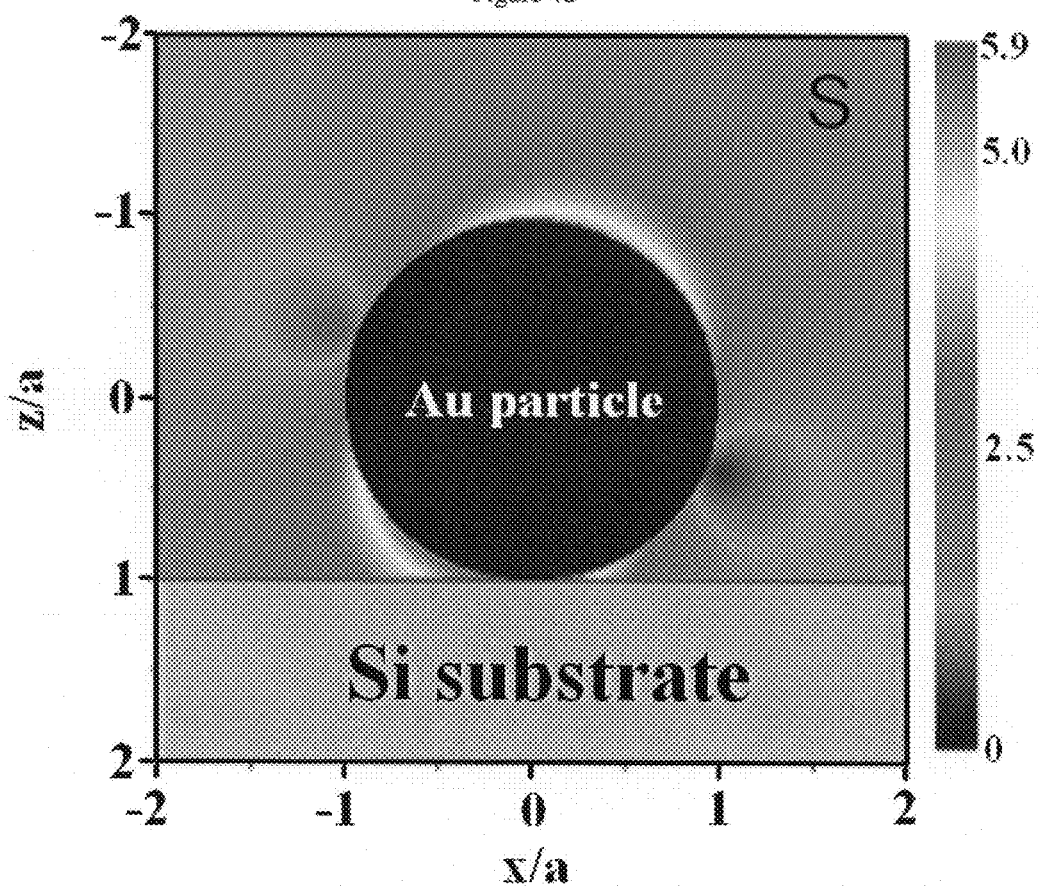

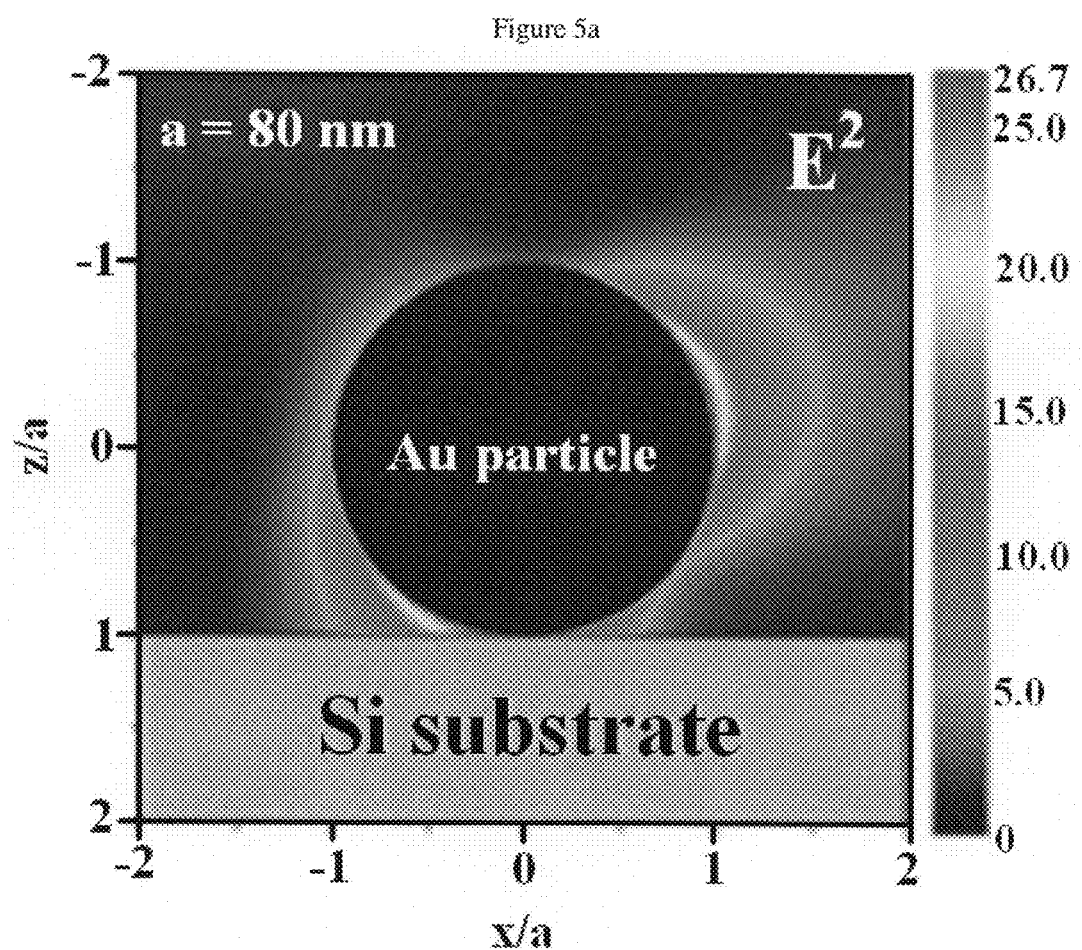

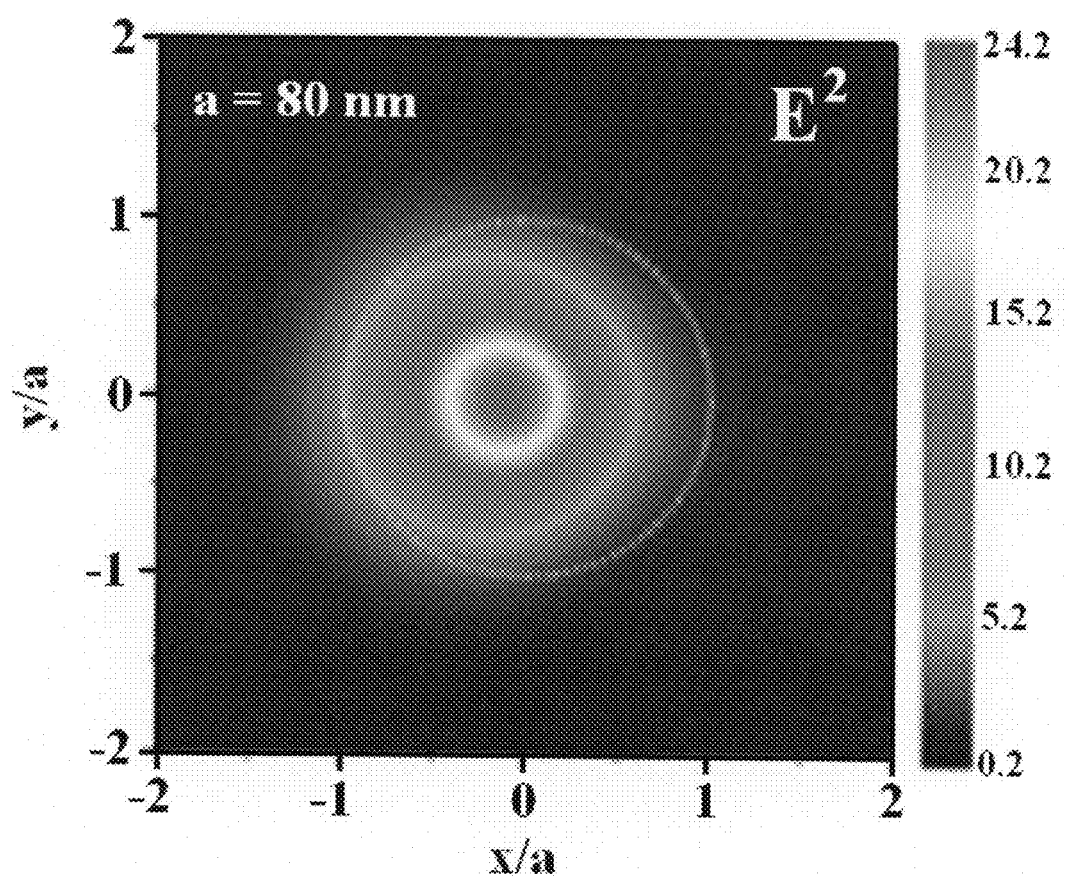

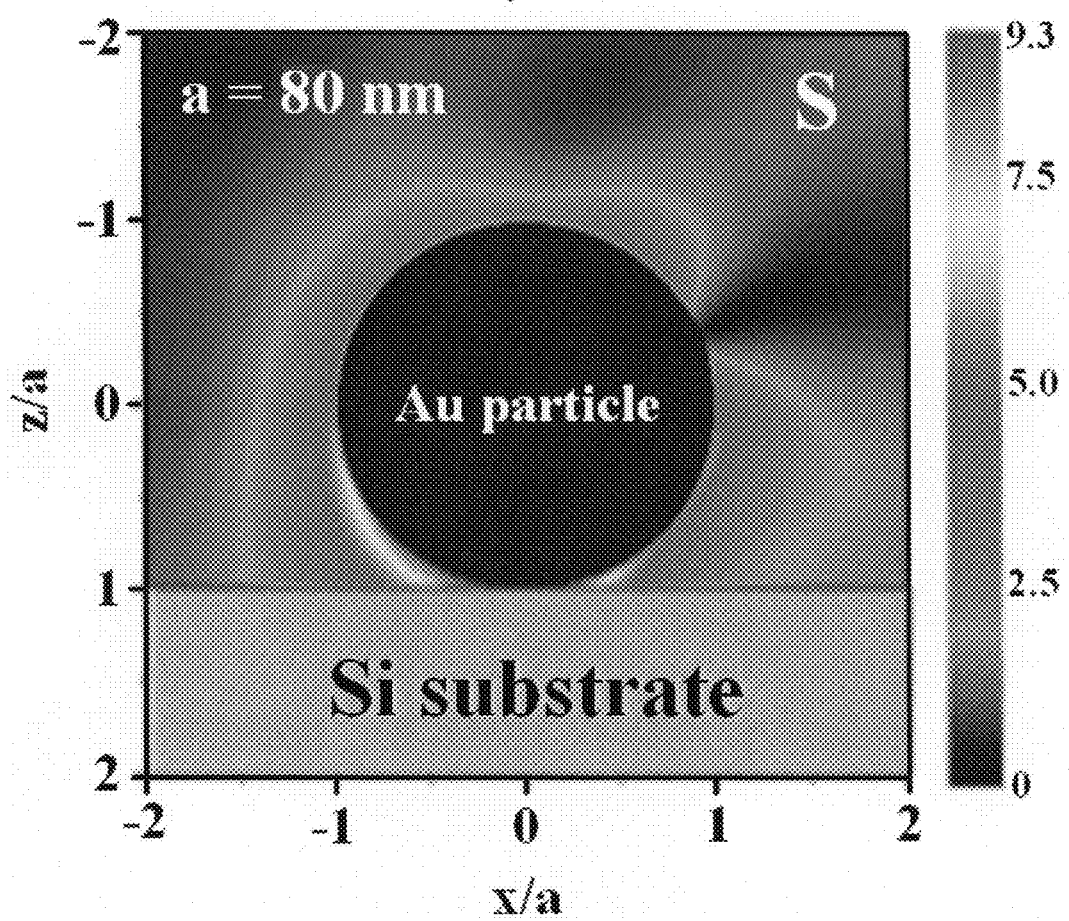

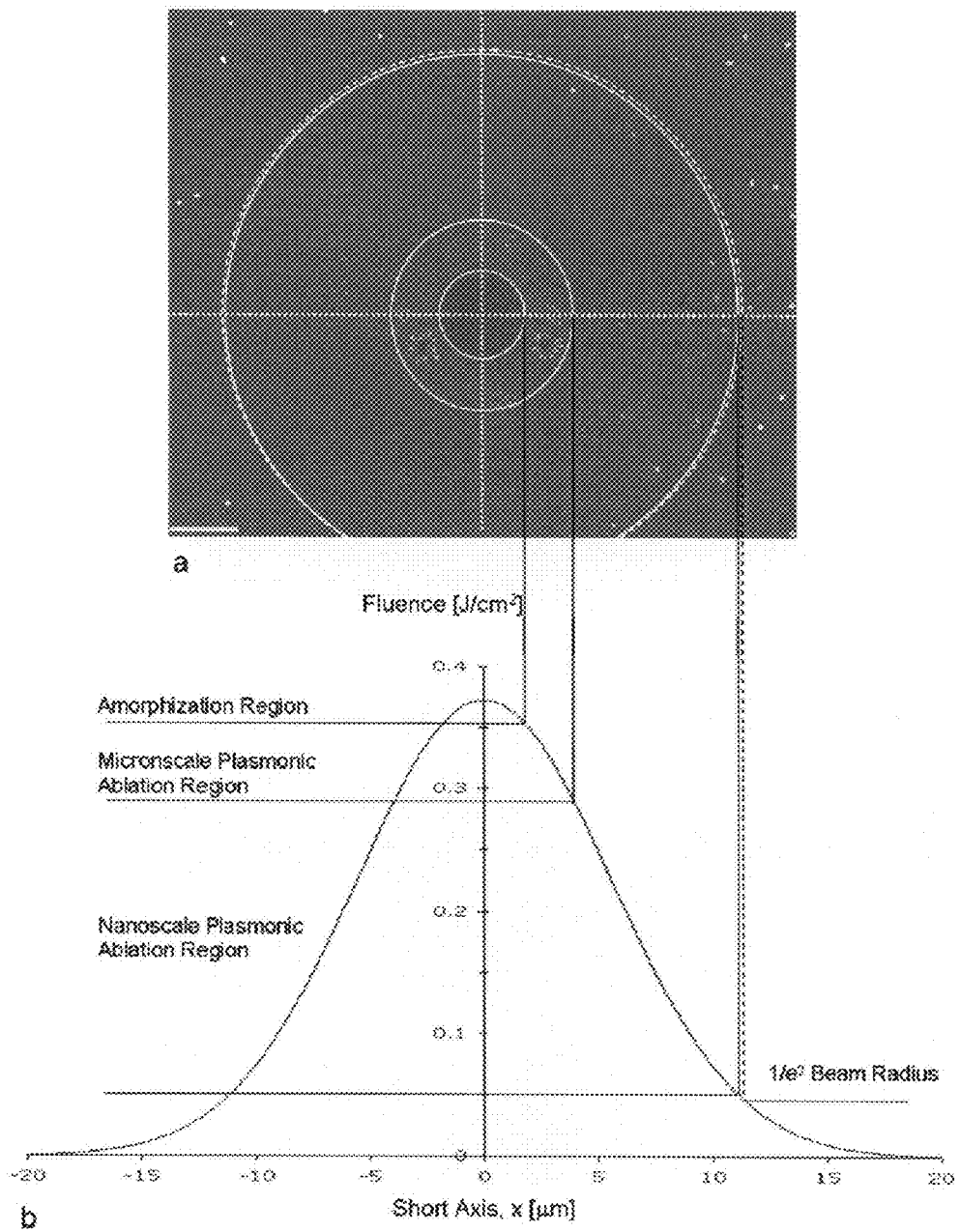

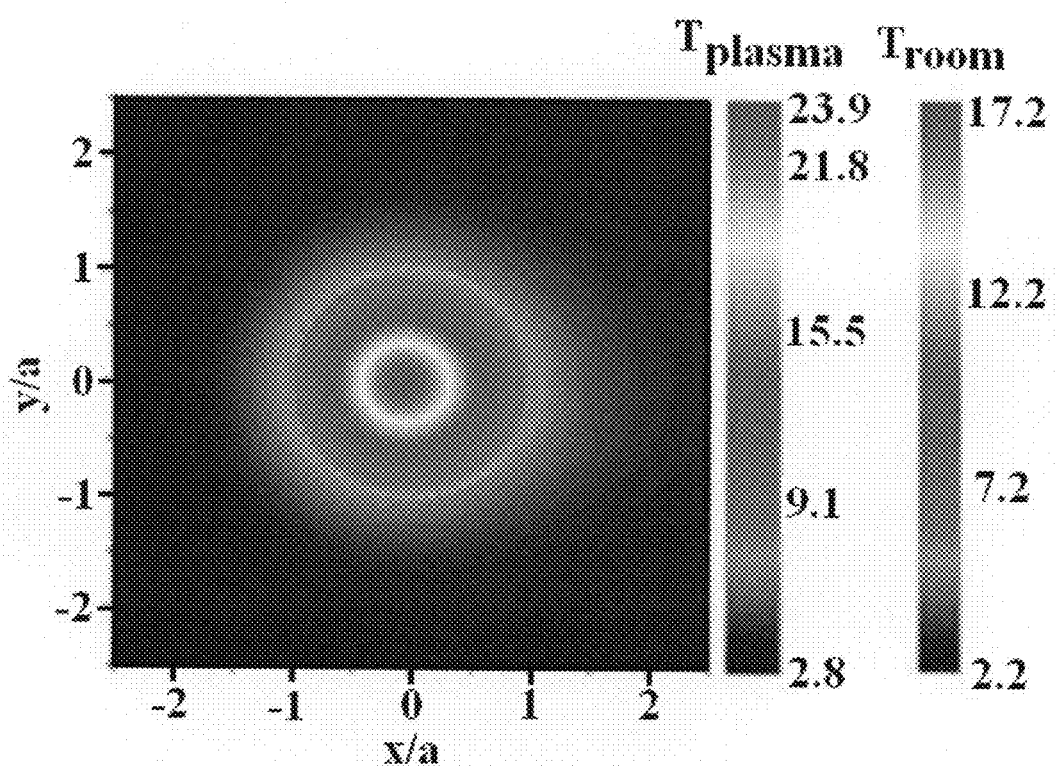

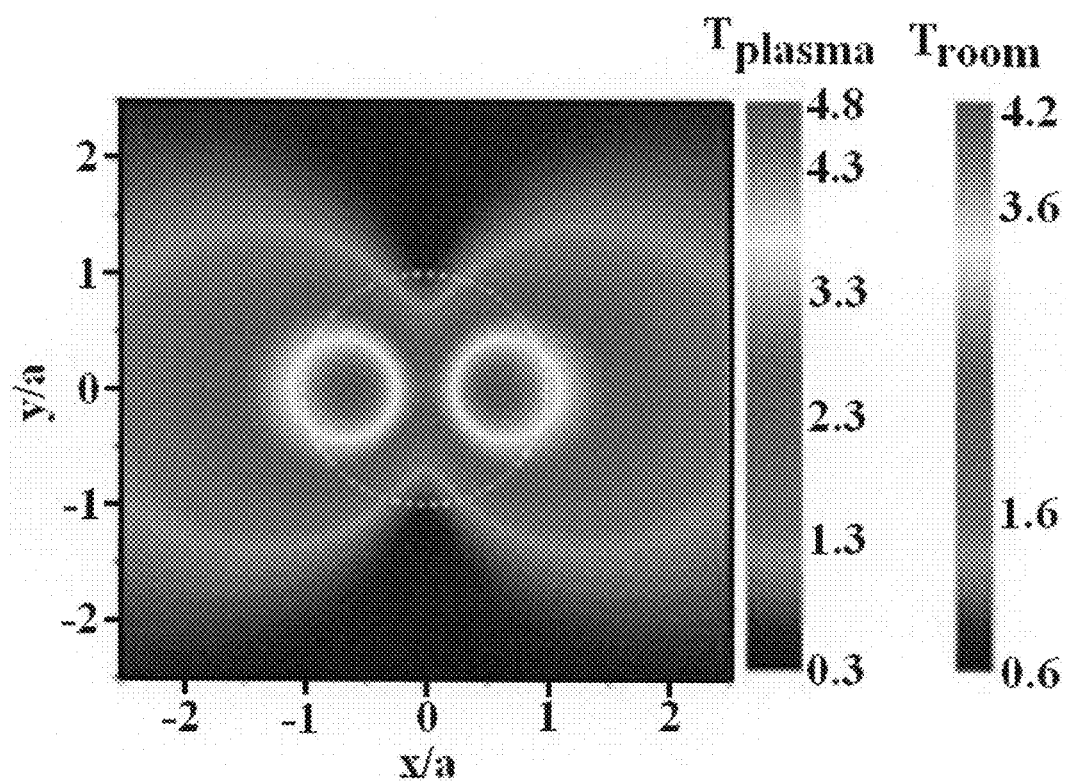

(a) before  (b) after

PLASMONIC LASER NANOABLATION METHODS

CROSS-REFERENCE TO RELATED APPLICATIONS

This application claims the benefit of U.S. Provisional Patent Application Ser. No. 60/953,316, filed Aug. 1, 2007, and U.S. Provisional Patent Application Ser. No. 60/971,377, filed Sep. 11, 2007, the entire disclosures of which are hereby incorporated by reference.

STATEMENT OF GOVERNMENT INTEREST

This invention was developed with support under Grant Numbers BES-0508266 and BES-0548673 awarded by the National Science Foundation and Grant Number RO3—CA125774-01 awarded by the National Institutes of Health. The U.S. government has certain rights in the invention.

BACKGROUND

Precision femtosecond laser microsurgery (FLMS) requires the use of tightly focused near-infrared femtosecond laser pulses for the precise manipulation of subcellular structures. To make these submicron ablations, femtosecond laser pulses need to be tightly focused with an expensive high numerical aperture lens. The femtosecond pulses provide high peak intensities and rapid deposition of energy into the target, ablating material before significant heating of the surrounding target occurs. This may be achieved because the pulse width is shorter than the thermal relaxation time of the target. As such, FLMS allows for submicron resolution. This technique, however, has inherent limitations: (1) the target needs to be located with submicron resolution and (2) the light diffraction limits the operation resolution to about half a micron. Many current techniques use highly absorbing metal particles to destroy surrounding tissue through heating effects to explosively melt them. These particles absorb a majority of light and release the energy as heat to the surrounding intercellular components during the heat transfer process, denaturing proteins and destroying intracellular components. This photothermal process increases the mean temperature of the exposed tissue, in some cases by more than approximately 50° C., which could cause complications and extensive damage in normal tissue.

SUMMARY

In certain embodiments, the present disclosure provides a method comprising: positioning a nanoparticle in proximity to a surface of a material; irradiating the nanoparticle with a laser tuned to the nanoparticle's plasmonic frequency; and allowing a near-field effect from the irradiated nanoparticle to photodamage the material.

In certain embodiments, the present disclosure provides a method comprising: positioning a nanoparticle in proximity to a surface of a material; irradiating the nanoparticle with a low peak power laser pulse; obtaining an image of the material; irradiating the nanoparticle with a laser tuned to the nanoparticle's plasmonic frequency; and allowing a near-field effect from the irradiated nanoparticle to photodamage the material.

The present disclosure is based, at least in part, on the observation that a purely scattering technique using nanoparticles can be harnessed to initiate plasma mediated photodamage to selectively remove material with nanoscale resolution. Such an approach has a number of advantages, including, among other things, extremely precise laser material removal while minimizing undesired heating effects, the use of single pulses to ablate and/or modify structures, which may not be possible using heating effects, and the use of low numerical aperture lens, which effectively lowers the cost of building a high precision tool and reduces the amount of time needed to focus the laser, as the nanoparticles themselves will in essence act like as a high numerical aperture lens.

The methods of the present disclosure, according to certain embodiments, utilize a novel femtosecond laser nano-ablation technique called Plasmonic Laser Nano-Ablation (PLN). The technique takes advantage of surface-enhanced plasmonic scattering of ultrashort laser pulses by nanoparticles to vaporize sub-cellular structures in attoliter volumes. The use of nanoparticles may overcome problems associated with current FLMS techniques and does not rely on heating for nanodisruption. In PLN, the particle acts as a "nano-lens," restricting laser light to the near-field of the particle, and only photodisrupting structures that are nanometers away. This eliminates the need for a tightly focused beam, while still achieving nanoscale resolution. Moreover, the enhanced scattering around the particles reduces the amount of required laser fluence. FIG. 1 provides a brief illustration of an embodiment of such a concept.

In certain embodiments, PLN also may be used to perform large-scale material removal on the nanoscale, for example, by using high-throughput techniques such as, but not limited to, microfluidic devices. While selective removal of material with nanoscale resolution can be performed using single 100 fs laser pulses, using kilohertz pulse rates may provide the ability to modify large surface volumes in extremely short time durations. In certain embodiments, well-defined structures may be produced by PLN in any solid material independent of excitation wavelength.

The methods of the present invention may provide a number of benefits over traditional ablation techniques. In certain embodiments, the methods of the present invention may improve the selectivity, for example, the methods of the present invention may limited the ablation to a desired area and/or reduce the ablation of material which is not desired to be ablated. In certain embodiments, the methods of the present invention may allow for the simultaneous imaging and selective material removal, as described in detail later. In certain embodiments, the methods of the present invention may provide a high throughput photomanipulation process, for example, the methods of the present invention may be capable of selective material removal for a greater number of samples that traditional ablation techniques in a specified amount of time. Applications of certain embodiments of the methods of the present invention include, but are not limited to, cancer cell removal, transfection (DNA, RNA, protein, siRNA, drugs), blood clot and atherosclerotic plaque removal, gene knockout (perturb DNA and chromatin), study basic biological pathways, nanolithographic technique, nanomachining, protein manipulation and inactivation, viral manipulation, and bacterial manipulation.

The methods of the present disclosure may be useful in engineering and basic science applications, including, but not limited to, nanomachining, nanolithography, fast-cellular processing for stem-cell separation, cancer applications (tumor removal and apoptosis initiation), nanoscale axotomy, molecular and genetic manipulation, and for both imaging and therapeutic purposes.

The features and advantages of the present invention will be readily apparent to those skilled in the art upon a reading of the description of the embodiments that follows.

DRAWINGS

Some specific example embodiments of the disclosure may be understood by referring, in part, to the following description and the accompanying drawings.

FIG. 1 illustrates an embodiment of the principle of high precision laser surgery by using: (a) tightly-focused femtosecond laser pulses and (b) enhanced electric field near metal nanoparticles.

FIG. 2 illustrates (a) the extinction of the 20 nm and 80 nm radius particles, (b) Mie simulations of enhanced electromagnetic fields around 20 nm, and (c) 80 nm radius isolated particles in cytoplasm at 780 nm wavelength (n=1.33).

FIG. 7 illustrates (a) an SEM image of nanoparticles deposited on silicon substrate after laser irradiation, and (b) the corresponding Gaussian distribution of the laser beam. A 190 mJ/cm$^2$ average fluence is directed orthogonally to the substrate (normal incidence). Several regions of ablation can be ascertained from the image. The scale bar is 3 µm.

FIG. 8 illustrates AFM images of nanocraters ablated by 150 nm gold nanoparticles on silicon (100) and corresponding cross sections as found along the white dotted line: (a) and (d) 88 mJ/cm$^2$ pulse fluence having p-polarization at 45° incident angle, (b) and (e) 58 mJ/cm$^2$ pulse fluence having normal incidence, and (c) and (f) 128 mJ/cm$^2$ pulse fluence having s-polarization at 45° incident angle. The scale bars are 200 nm.

Figure 9:
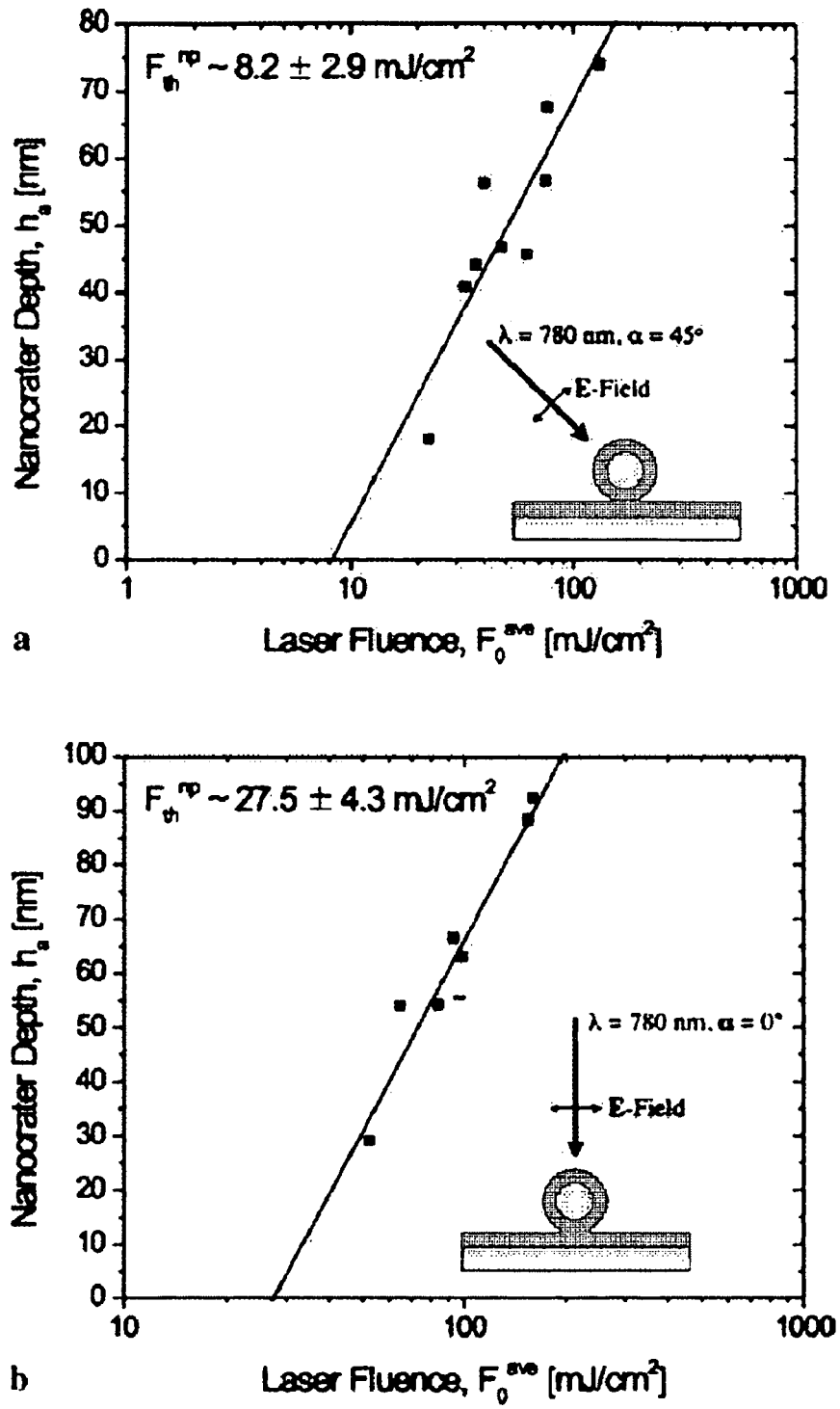
Figure 9:
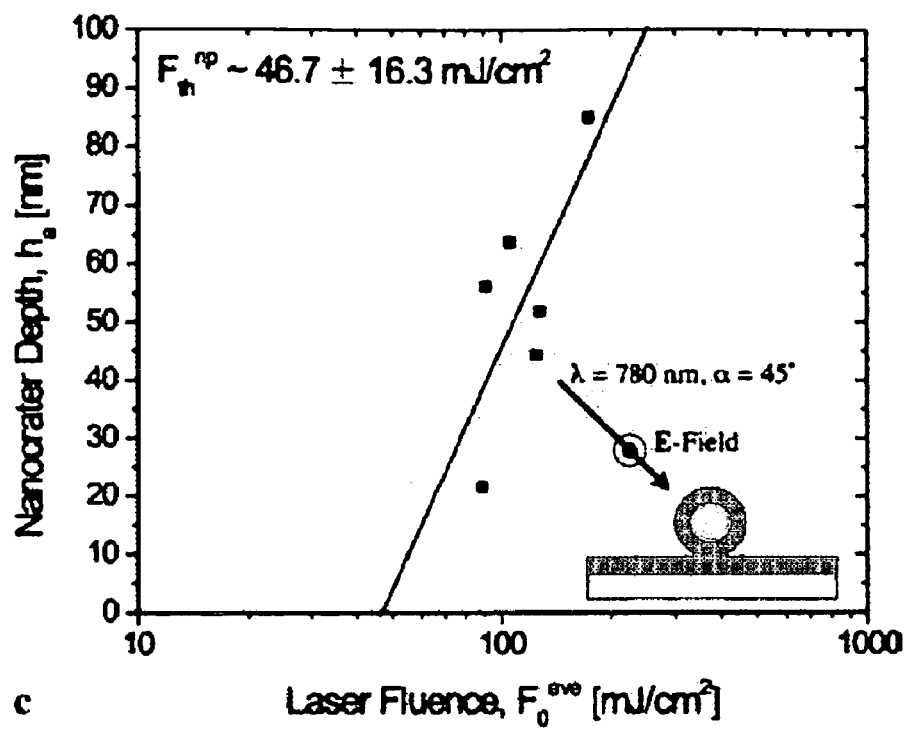

FIG. 9 illustrates crater depths generated by single 150 nm gold particles measured at various laser fluences. The depths of the ablation craters are plotted as a function of the laser fluence. Extrapolation of the linear fit to zero provides the enhanced sing-shot ablation threshold. Plots for three different polarizations types were generated: (a) p-polarization at 45° incident angle, (b) normal incidence, and (c) s-polarization at 45° incident angle.

Figure 10C:
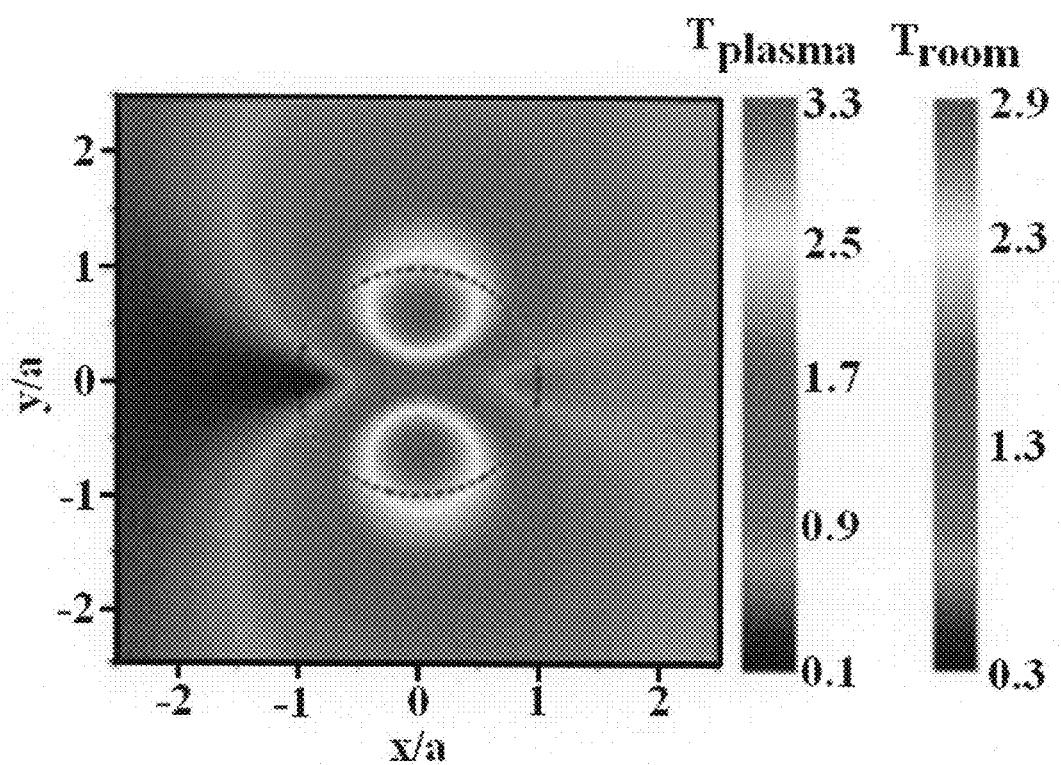

FIG. 10 illustrates calculated field intensity along the substrate surface, which is based on the solution of the boundary-value problem for a spherical particle on a flat semi-infinite substrate. The 150 nm particle is labeled as the dotted circle. $T_{plasma}$ and $T_{room}$ describe the field enhancement with and without the addition of the low density plasma generated along the silicon surface, respectively. (a) p-polarization at 45° incident angle, (b) normal incidence, and (c) s-polarization at 45° incident angle.

Figure 11A:
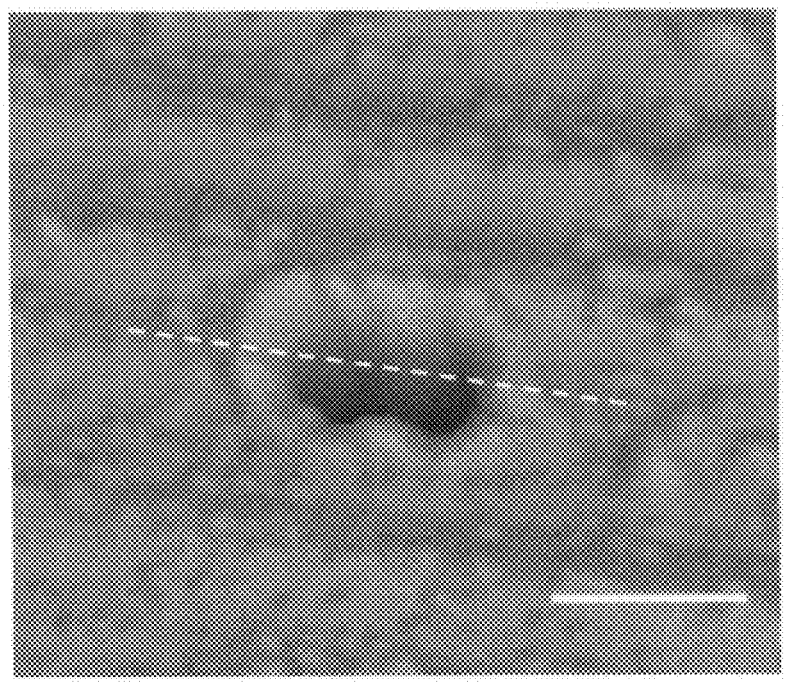
Figure 11B:
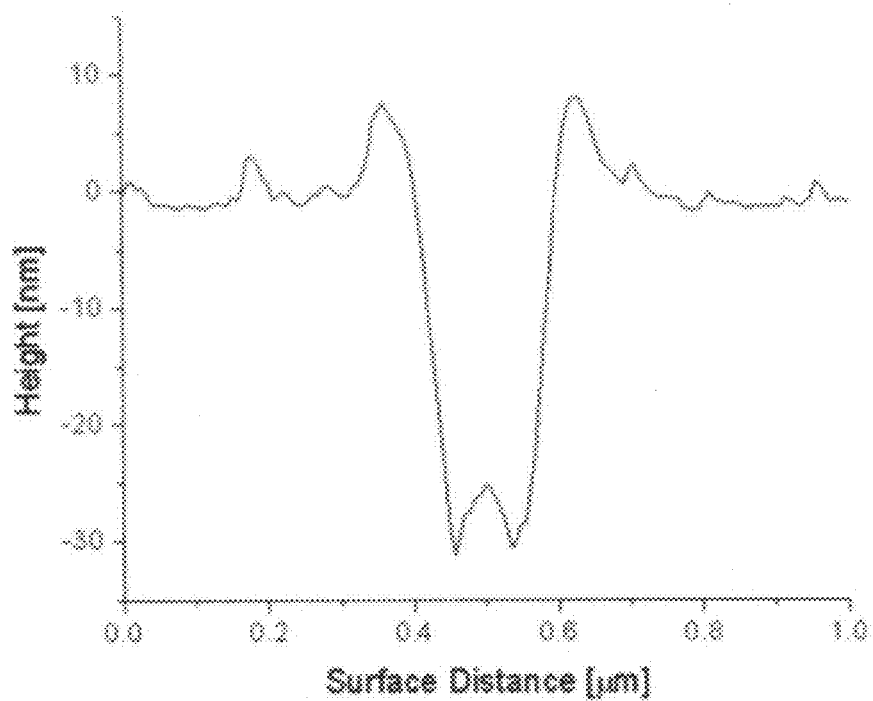

FIG. 11 illustrates (a) AFM image of nanoparticle-assisted ablation of the borosilicate glass surface by an 80 nm gold nanosphere. The intense scattering of the ultrafast pulse along the dipole caused ablation of the borosilicate surface. Ablation was performed with 1.2 J/cm$^2$ pulse fluence at normal incidence. (b) Profile of the nanoparticle/pit structure as seen along the white dotted line. The scale bar is 200 nm.

Figure 12:
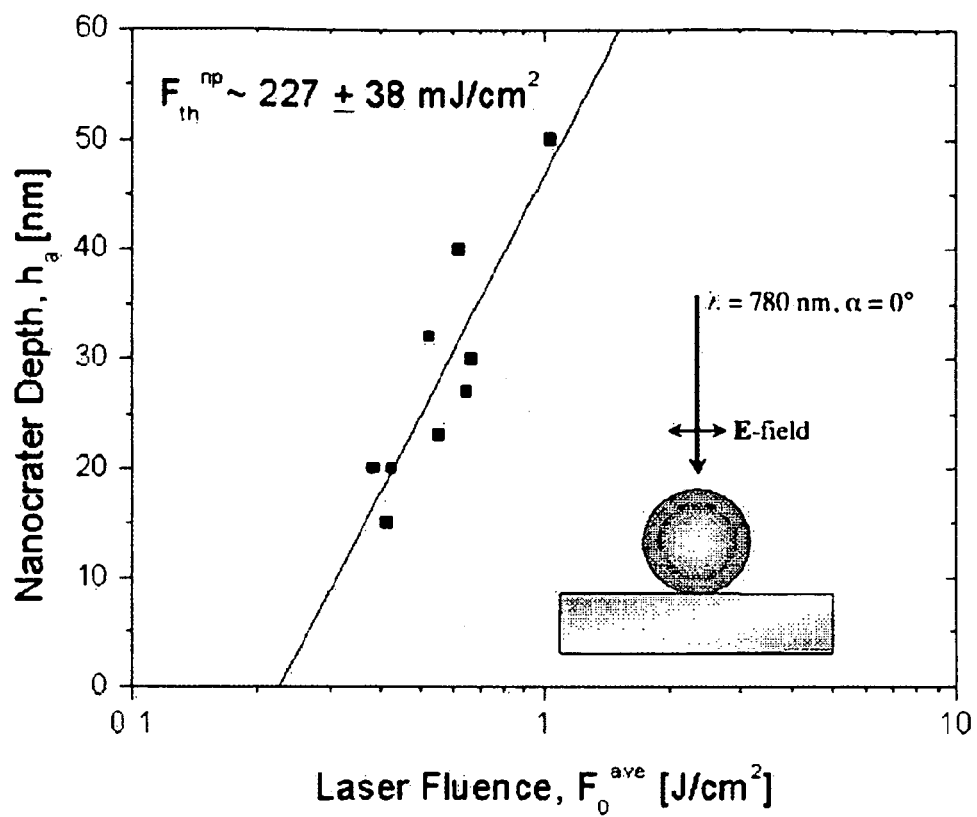

FIG. 12 illustrates crater depths generated by single 80 nm gold particles measured at various laser fluences. The depths of the ablation craters are plotted as a function of the laser fluence. Extrapolation of the linear fit to zero provides the enhanced single-shot ablation threshold for single particle ablation. Craters were generated with irradiation at normal incidence.

Figure 13:
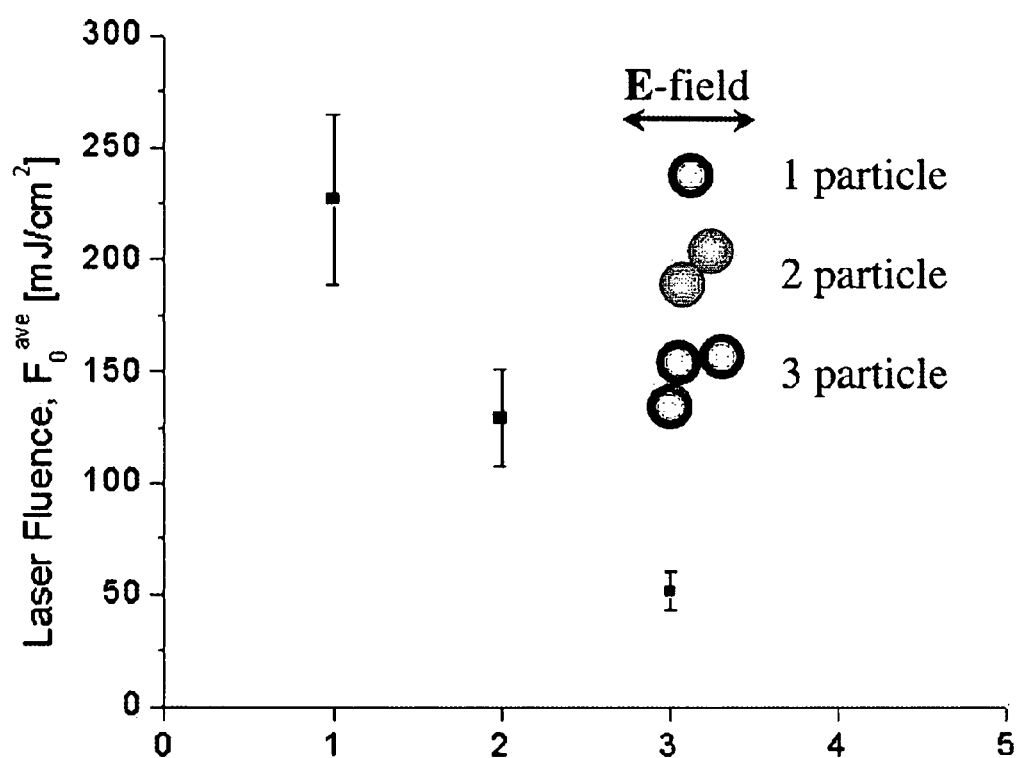

FIG. 13 illustrates the measured multiple particle ablation threshold. Aggregates of one-, two-, and three-particles oriented at a 45° to the incident electric field were studied. Their corresponding enhanced ablation threshold were plotted to show the threshold fluence dependency on aggregate size.

Figure 14:
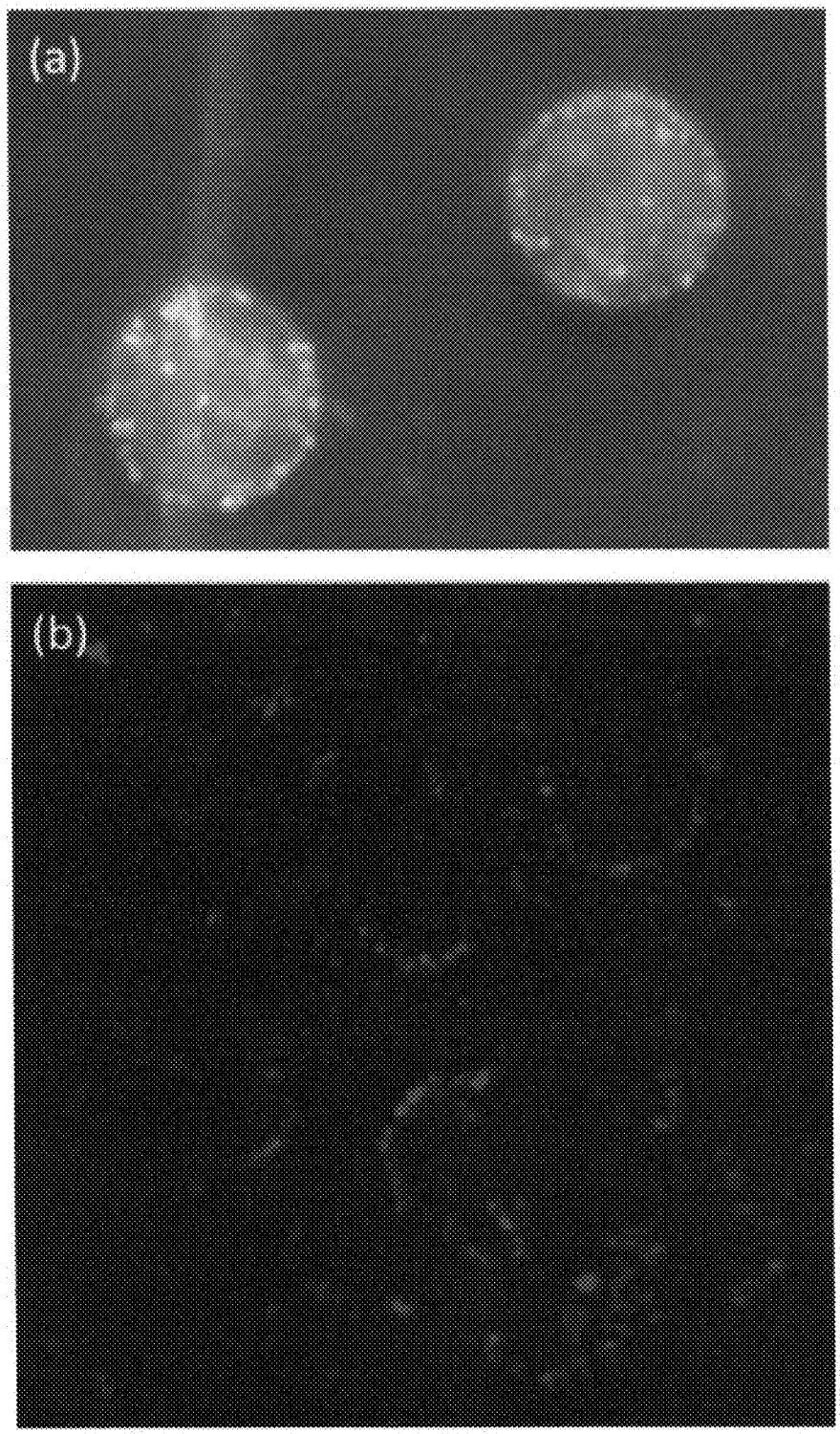
Figure 15:
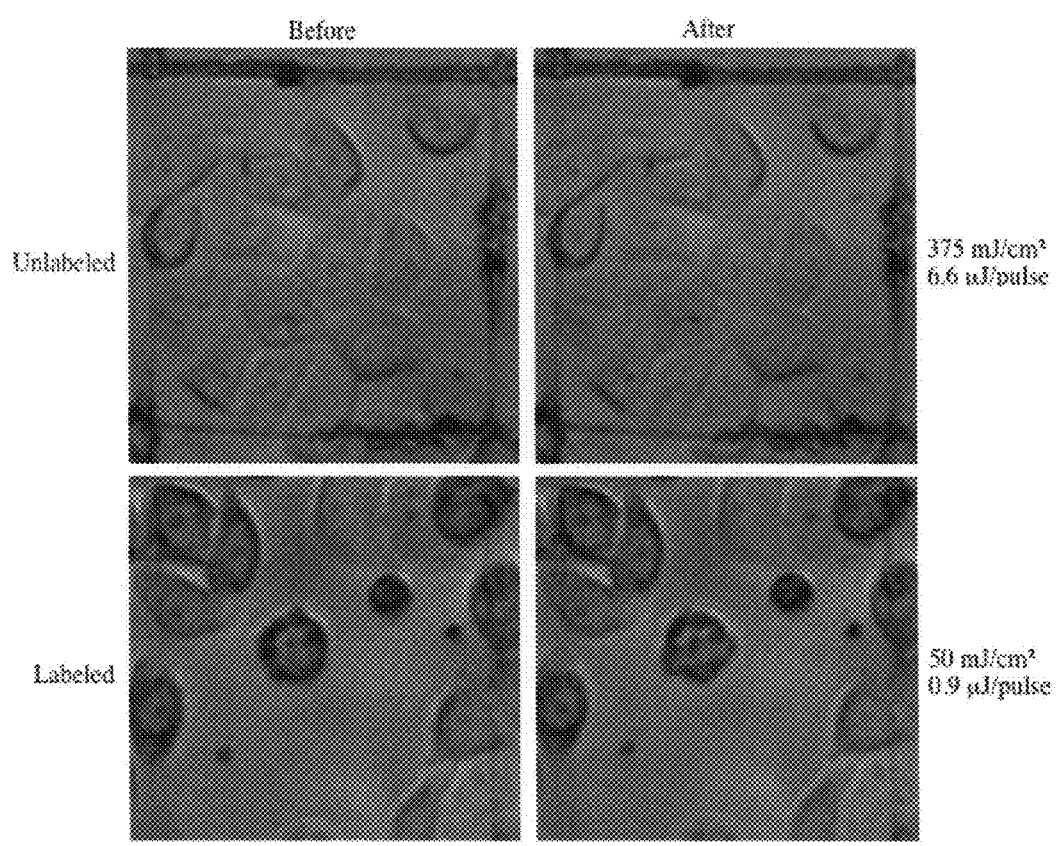

FIG. 14 shows optical images of MDA-MB-468 epithelial breast cancer cells labeled with Anti-EGFR gold bioconjugates using (a) dark field and (b) mulitphoton microscopy FIG. 15 shows epiluminescent images of MDA-MB-468 cells before and after irradiation. There is a reduction of 7-8 times in amount of fluence necessary to disrupt the cell membrane.

Figure 16:
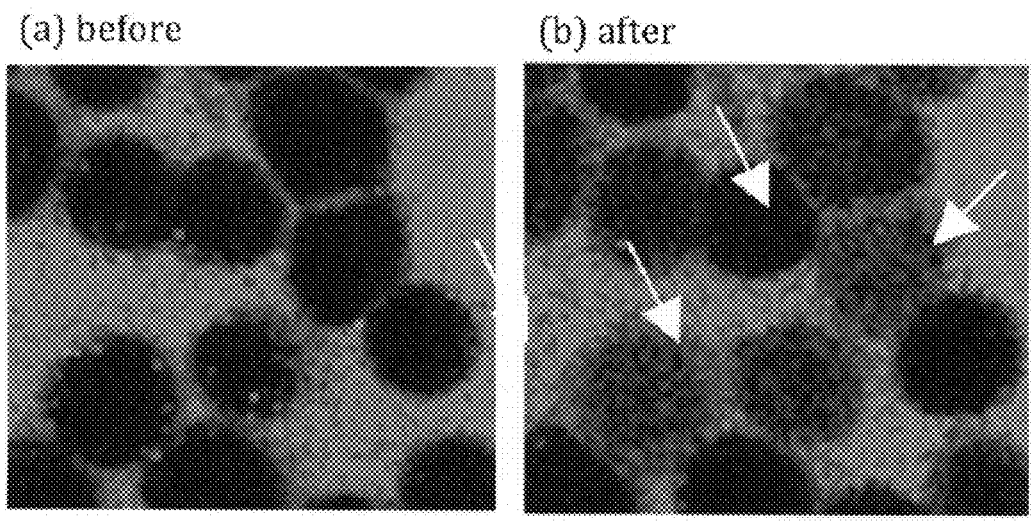

FIG. 16 shows multiphoton images of a MDA-MB-468 labeled cells (a) before and (b) after irradiation. Nanoparticle labeling along cell membrane is shown in red and 10 kDa FITC-Dextran contained within the extracellular space in green. There is a reduction of 33 times in the amount of laser fluence necessary to disrupt the cellular membrane, which is visualized by the influx of FITC-Dextran into cell after irradiation.

Figure 17:
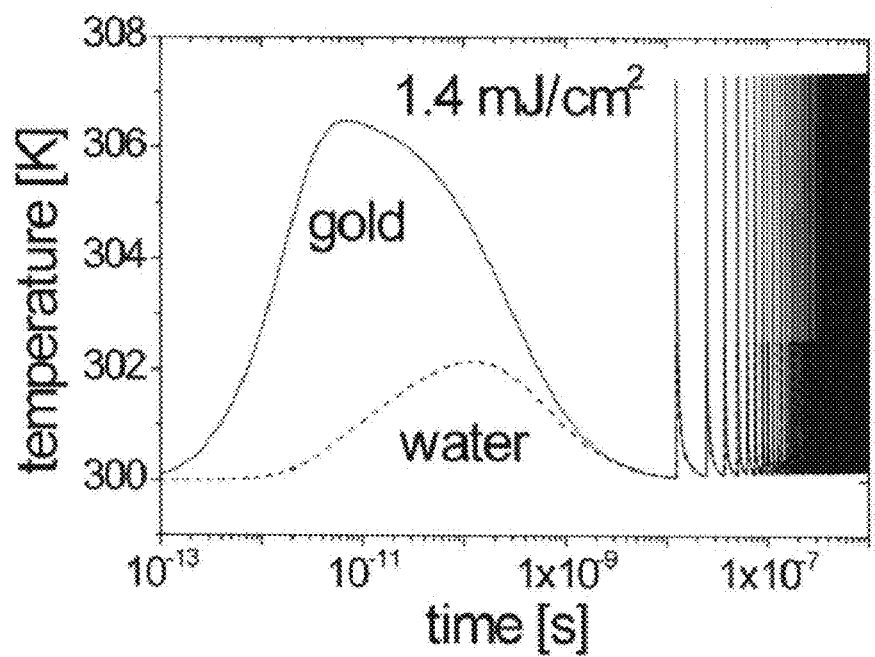

FIG. 17 shows femtosecond laser heating process of 50 nm gold nanosphere with multiple laser pulses. The temporal temperature profile demonstrates that at 1.4 mJ/cm$^2$ there is minimal heating of both the particle and its surrounding water.

Figure 18:
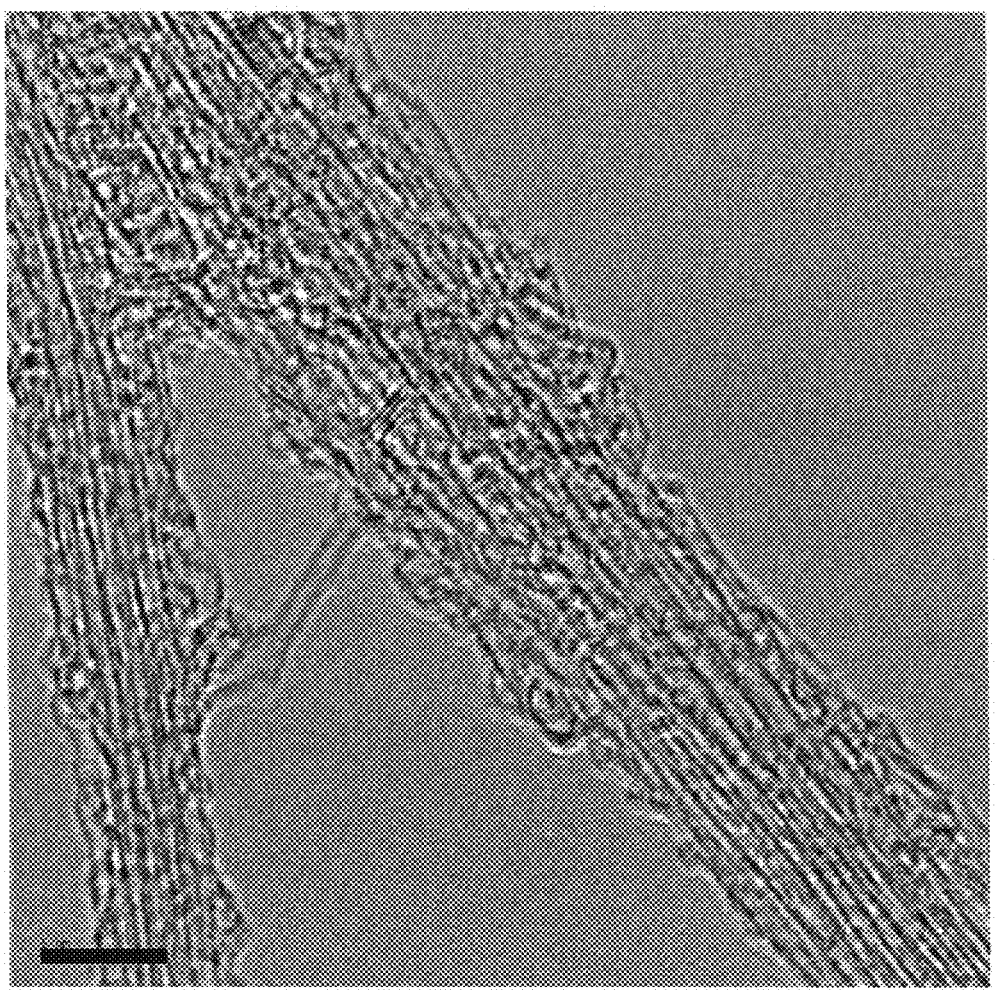

FIG. 18 shows a TEM image of SWCNT bundles after oxidation and ultrasonication processes. Scale bar is 5 nm.

Figure 19:
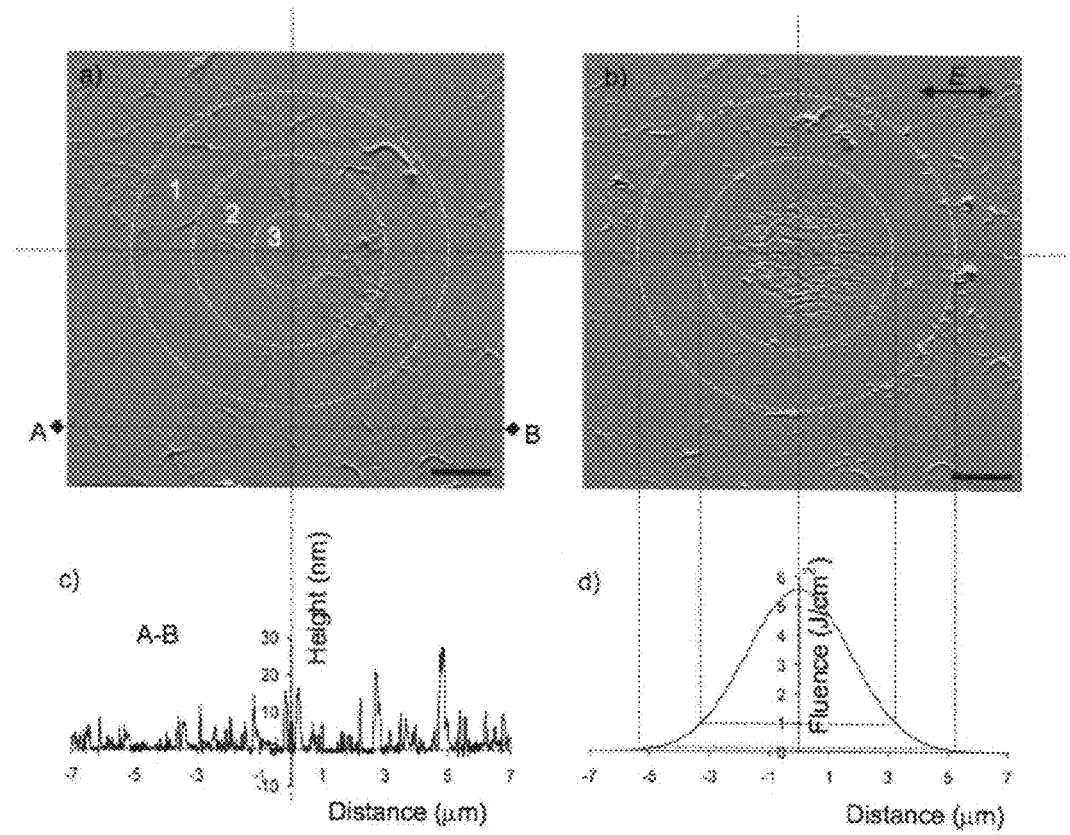

FIG. 19 shows AFM images of SWCNTs deposited on the glass substrate before (a) and after (b) fs-laser pulse irradiation. The area within the large circle indicates the region where SWCNTs disappeared. Glass ablation at the nanoscale and microscale takes place within the smaller circles, No. 2 and 3, respectively. The corresponding distribution of local laser fluence is plotted in the Gaussian curve in (d). The cross-sectional profile along A-B is plotted in (c). Scale bars are 2 mm.

Figure 20:
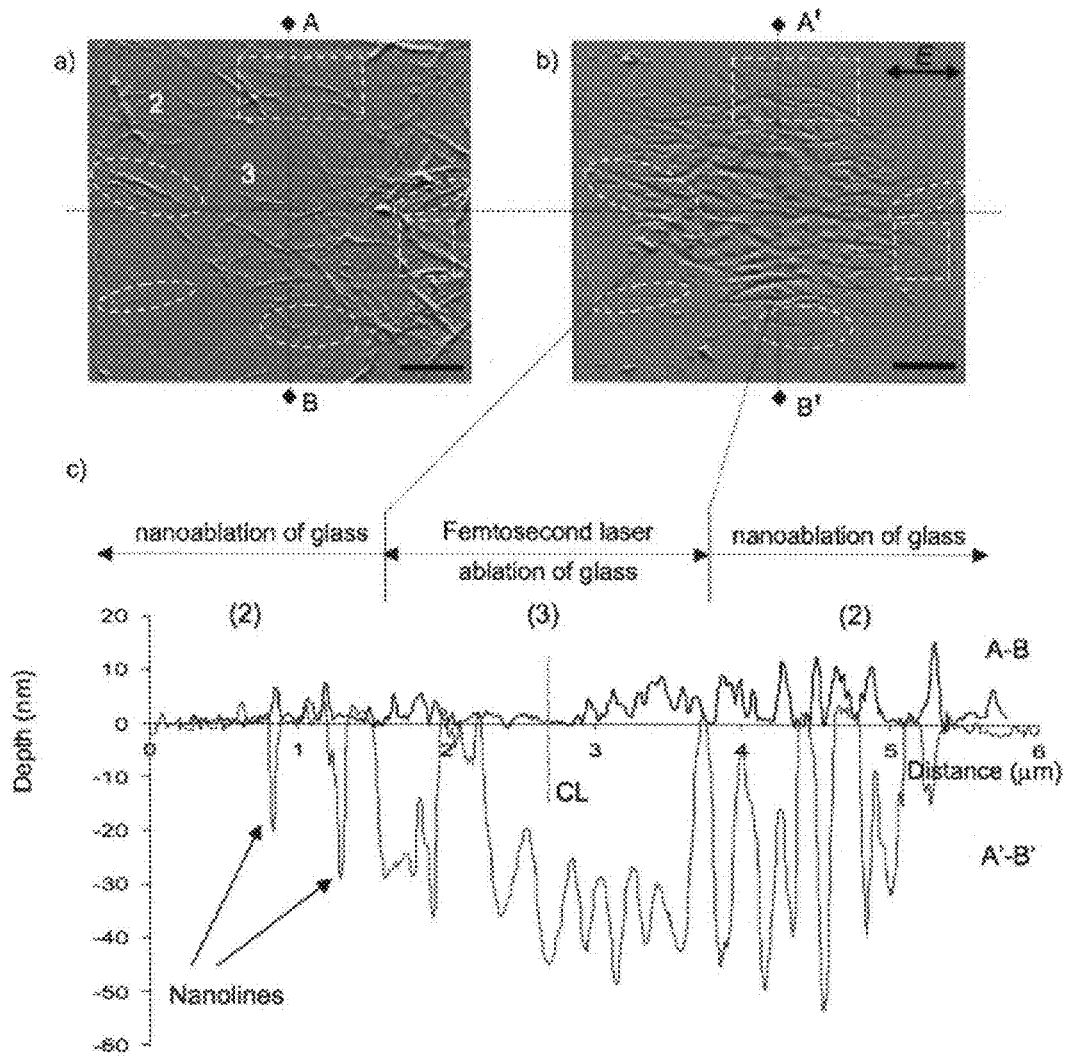

FIG. 20 shows magnified AFM images of the region within two small circles presented in FIG. 17 before (a) and after (b) ablation. Several dotted ellipses and rectangles are drawn to highlight that nanolines are directly created beneath the SWCNTs. Scale bars are 1 mm. (c) The cross-sectional profile along A-B and A'-B'.

Figure 21:
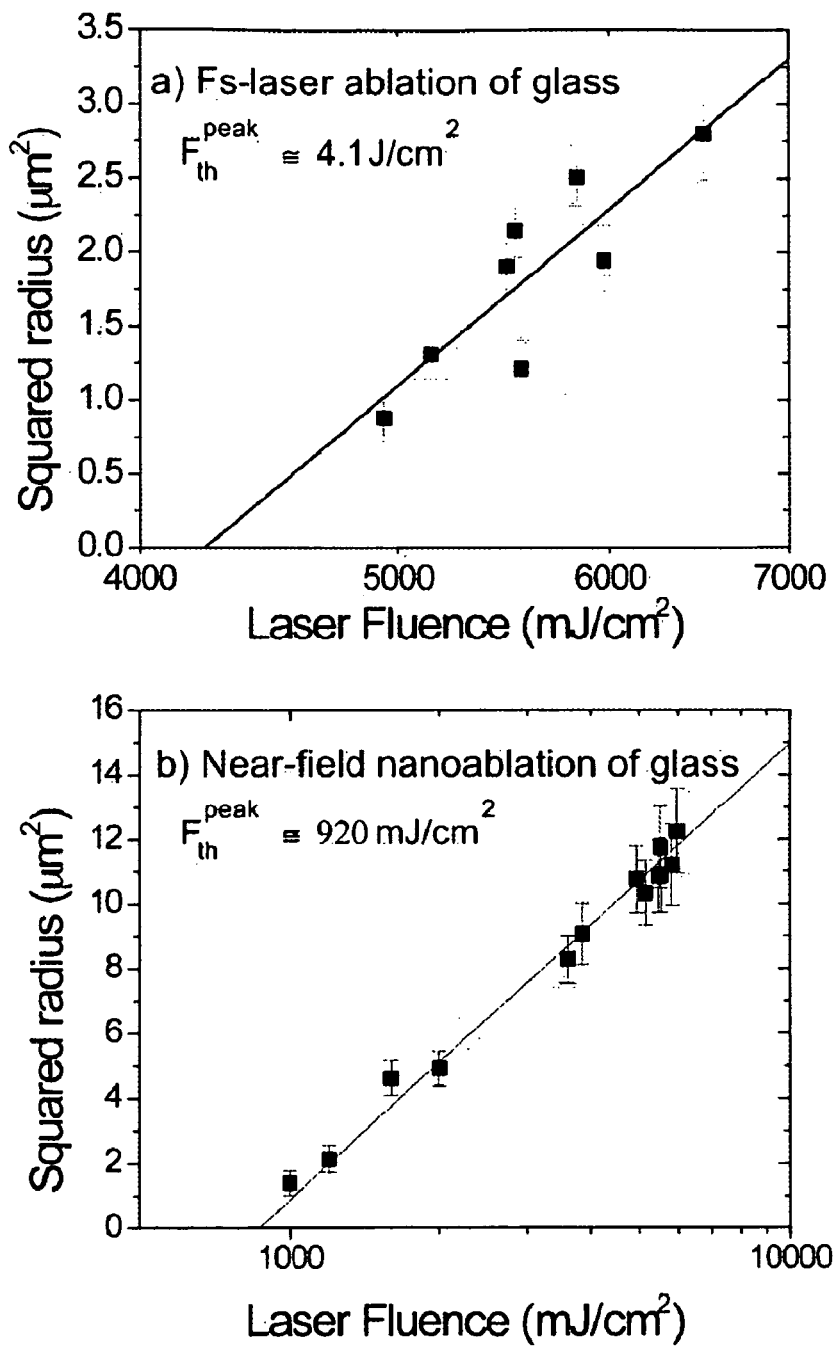

FIG. 21 shows a) Single-shot fs-laser ablation of glass, b) nanoablation of glass, and c) fs-laser ablation of SWCNT bundles. The plots show the linear relation between the squared radius of the areas (circles No. 1, 2, and 3) and the logarithmic of the local laser fluence in accordance with Eq. 5. The extrapolations to zero provide the single pulse thresholds. The error bars represent the uncertainty of the radius measurement.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure provides, according to certain embodiments, a method comprising positioning a nanoparticle in proximity to a surface of a material; irradiating the nanoparticle with a laser tuned close to the nanoparticle's plasmonic frequency; and allowing a near-field effect from the irradiated nanoparticle to photodamage the material.

The present disclosure provides, according to certain embodiments, a method comprising: positioning a nanoparticle in proximity to a surface of a material; irradiating the nanoparticle with a low peak power laser pulse; obtaining an image of the material; irradiating the nanoparticle with a laser tuned to the nanoparticle's plasmonic frequency; and allowing a near-field effect from the irradiated nanoparticle to photodamage the material.

The method uses Plasmonic Laser Nanoablation (PLN), in which the large enhancement of laser pulses in the vicinity of nanoparticles is used to selectively remove material with nanoscale resolution. When the laser frequency is tuned to the plasmonic frequency of a nanoparticle, the nanoparticle will efficiently collect light from a region significantly greater than its geometrical boundary and scatter it onto the region immediately surrounding the particle. The nanoparticle will act like a "nanolens," restricting the light to a subwavelength focal region in the particle near-field and described by the induced dipole. The intensity of near-field scattered wave drops off at a rate approximately equal to $(a/R)^{12}$, where a is the particle radius and R is the observation position. The amplified electric field in this region, can cause photodamage with nanoscale precision to targets. Reduction in the interaction volume to the nanoscale allows for a substantial reduction in the pulse fluence. Consequentially, there will be almost negligible mechanical and thermal effects on surrounding structures, and the shock zone will only extend a few nanometers beyond the ablation "nano-domain" sites. This leads to, among other things, the ability to perform nanoscale photodamage of materials, as well as large scale ablation using high-throughput techniques.

The lasers suitable for use in the methods of the present invention may be any laser capable of emitting light of a desired wavelength so as to irradiate the nanoparticles useful in the methods of the present invention. Such lasers may be femtosecond, picosecond, or nanosecond pulse lasers. One example of the lasers useful in the methods of the present invention is a femtosecond Ti:sapphire laser system commercially available from SpectraPhysics of Mountain View, Calif.

In general, suitable nanoparticles may have any desired geometry. For example, the nanoparticles may be spherical or anisotropic (e.g. rod, tube, ellipsoid, triangle, wire, rice, star, shell, cage, and their clusters). Spherical nanoparticles generally have the lowest overall enhancement. Having sharp edges or irregularities on the particle surface may increase the overall enhancement, and especially strong enhancements may be found at the sharp edges. Suitable nanoparticles can be composed of all noble-metal types (e.g., gold, silver, and copper) or from composites of two or more noble-metals, which may allow a large range of enhancements and excitation wavelengths. Suitable nanoparticles also may be composed of carbon, for example, carbon nanotubes (single- or multi-walled), fullerenes, and carbon dots, and other carbon-based nanostructures. The nanoparticles may be formed from a single material or two or more materials (heterodyne systems or alloys). Nanoparticle geometry, size, and composition may affect near-field scattering properties and can be chosen based on the properties desired and for a particular application. For example, gold nanospheres are suited to biological application because, among other things, they produce cellular poration with low laser fluences and little cell toxicity. Silver nanoparticles, on the other hand, have a stronger near-field scatter cross-section then gold, but are not as biocompatible, and therefore silver nanoparticles may be more suited to applications such as, for example, nanoablation of solid materials such as, but not limited to, silicon.

For biological applications, the nanoparticle may be targeted to specific cellular sites by conjugating the particle to antibody- or peptide-mediated receptors, subcellular organelles, and/or DNA and/or RNA base pairs. Such nanoparticles may be used to locally disrupt intracellular membranes and molecules in the cell without damaging other intracellular components, which offers an extremely precise form of laser surgery. In addition, the ability to tune the scattering properties of the nanoparticle allows performance of cellular ablation in the near-infrared (NIR) wavelength regime. NIR light is not absorbed by biological tissues and can penetrate deep into tissue structures, which allows for light interaction only at zones mediated by nanoparticles. Mie Theory may be utilized to determine the size of nanoparticle that exhibits the greatest near-field scattering enhancement without having any significant heating. Examples of suitable nanoparticles for biological applications include, but are not limited to, gold nanoparticles and single walled carbon nanotubes. In certain embodiments, the nanoparticle may be attached to the material to be ablated by any suitable means known to one of ordinary skill in the art.

In some embodiments, the methods of the present disclosure may be used for both imaging and therapeutic purposes by, for example, using the nanoparticles as both a contrast agent and a modification tool. Using low peak power pulses, the nanoparticles can be used to enhance imaging and identify tagged areas before modification. By ramping the laser's peak power, the particle can then be used for material modification.

Figure 2A:
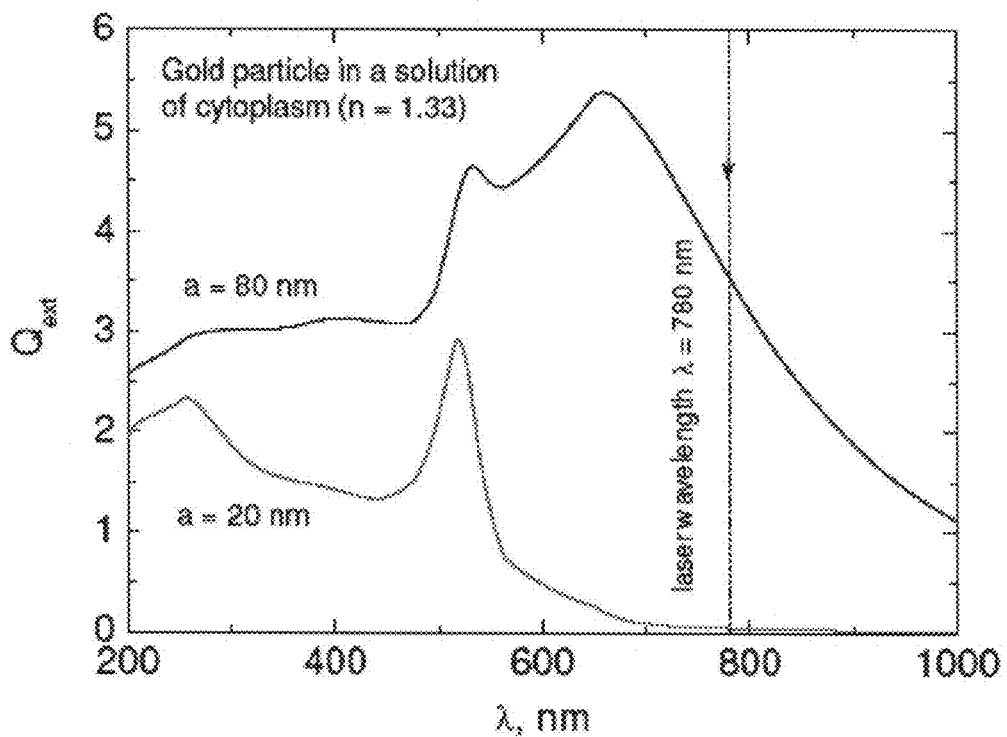

Models may be created for single particle systems and particles directly interacting with an underlying substrate. Specifically, a 3D Mie model may be developed to observe the magnitude and direction of the dipole field near the nanoparticle as it interacts with an underlying substrate. It is well known that for small spherical gold particles (~20 nm diameter) in the far field, the extinction peak is highly localized at roughly 520 nm wavelength. At this wavelength, both the absorption and scattering properties of the particle are very strong. If the observation wavelength is moved off the peak, both scattering and absorption decrease dramatically to negligible amounts. As the particle size increases, the extinction peak redshifts and broadens. Interesting, though, is that the absorption peak only slightly redshifts, while the scattering peak significantly redshifts, moving into the near-infrared wavelengths. To show this phenomenon, the extinction coefficient with respect to wavelength may be plotted for two different particle sizes in a cytoplasmic solution (as shown in FIG. 2a): 40 nm and 160 nm in diameter. As expected, the 40 nm particle exhibits pure dipolar scattering properties, peaking approximately at a wavelength of 530 nm. The peak is sharply defined and the full width at half maximum (FWHM) of the function is approximately 25 nm. As the particle gets larger, the dipole peak broadens and redshifts. With the 160 nm particle, the dipole peak is shifted to approximately 660 nm and its FWHM is 100 nm. In addition to the dipole peak, there is now a secondary peak located at the original wavelength of 530 nm. This peak, having a FWHM of 25 nm, represents the quadrapole, which forms when the excitation light cannot homogeneously polarize the nanoparticle, leading to retardation effects. This initial simulation was performed in the far field of the particle, where the far-field parameters consist of the electric field components that are perpendicular to the radial component, $E_\theta$ and $E_\phi$.

Figure 3:
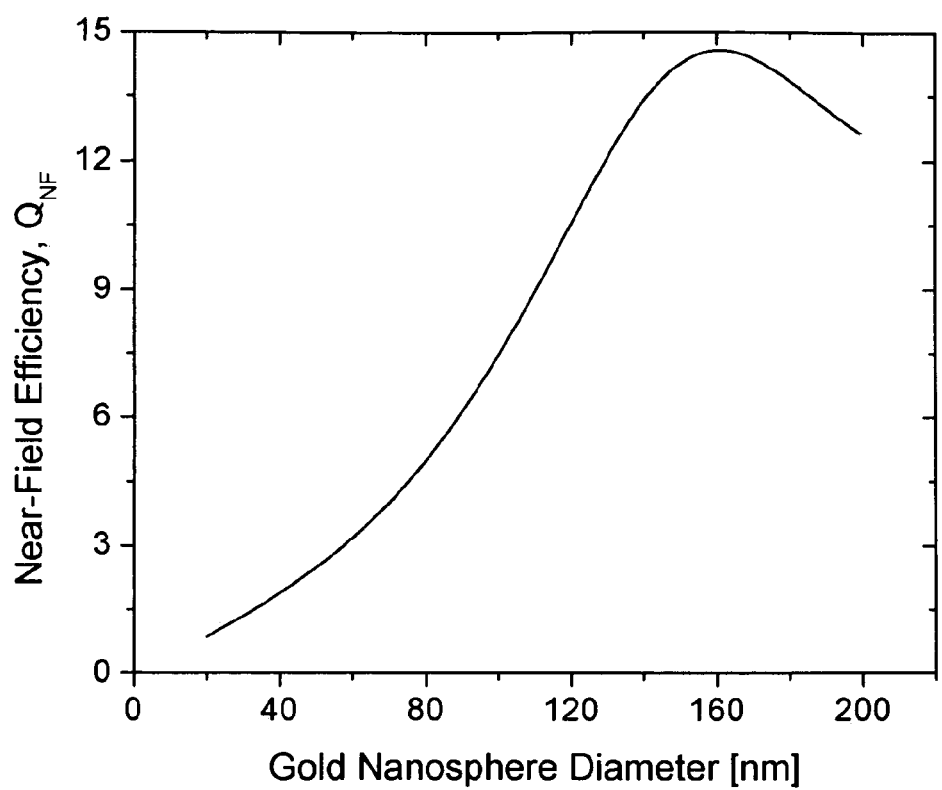
FIG. 3 illustrates the estimated near-field scattering efficiency, $Q_{NF}$, of gold nanospheres in air as a function of particle diameter.

Thus, to determine the appropriate particle size to produce the largest field enhancement at 780 nm, we estimated the near-field scattering efficiency, $Q_{NF}$, of a gold particle embedded in air as a function of its radius. $Q_{NF}$ is a measure of the sphere's ability to convert the incident electric field intensity into a near-field intensity. This quantity, which is proportional to the square of the scattered electric field on the particle surface, $E_s$, is given by $$Q_{NF} = \frac{R^2}{\pi a^2} \int_0^{2\pi} \int_0^{\pi} E_s \cdot E_s^* \sin\theta \, d\theta \, d\phi \Big|_{R=a} \quad (1)$$

where R defines a spherical surface over which the integral is evaluated and a is the particle radius. The near-field quantity consists of all three components of the electric field vector. The angular components, $E_\theta$ and $E_\phi$, are perpendicular to the particle surface, while the radial component, $E_R$, lies normal to the surface. The $E_R$ component, which is proportional to $R^{-2}$ dominates the scattered field, yielding large fields in the vicinity of the particle. Relating the near field to the far field, we find that the near field scattering efficiency decreases to the asymptotic value of the far-field scattering term, giving $Q_{Sca} = \lim_{R>>a} Q_{NF}$. For a given set of sphere parameters, $Q_{NF}$ will be greater than unity, which implies the sphere acts as a field intensifier. This yields local fields larger than that incident on the particle. FIG. 3 summarizes the calculations using Eq. 1. The plot indicates that the near-field enhancement of a spherical gold particle in air is greatest for particles 150-170 nm in diameter at the 780 nm wavelength. As the particle size increases, phase retardation in electron oscillations leads to multipole resonances red-shift the maximal $Q_{NF}$ to longer wavelengths. While having a larger near-field enhancement, 150 nm particles have reduced absorption effects. The dielectric function of gold material reduces with longer wavelengths due to the reduced d-level to sp-band electronic transitions, giving significantly reduced absorption effects. Through theoretical Mie calculations we expect 600 times more incident energy to be scattered in the particle near-field than to be absorbed. Since 150 nm gold nanospheres exhibit the largest scattering properties in the near-field with minimal absorption effects, they are the best candidates among the gold nanospheres for plasmonic ablation.

To understand the direction and shape of the scattered electric field in the near field, the three-dimensional electromagnetic scattering properties of a spherical gold nanoparticle may be mapped. Numerical simulations may be performed to observe the field enhancement around an isolated nanoparticle in a solution of cytoplasm (n=1.33) when irradiated with 780 nm light. FIG. 2 illustrates the field enhancement due to particle size. The 40 nm diameter particle exhibits pure dipole scattering with a maximum intensity enhancement of 13.5. By increasing the particle radius by a factor of 4, the maximum intensity enhancement approximately doubles. Further observation shows that the two lobes of the dipole are not along the same plane, but rather displaced by approximately 30°. This is caused by the presence of the quadrapole. If the particle is irradiated with 520 nm light, the scattered light would appear in four distinct lobes. Since the excitation wavelength coincides more with the dipole, the scattered light will only occur in two lobes. Though, the effect of the quadrapole will still be felt and each lobe will be displaced from the dipolar plane.

Figure 4A:
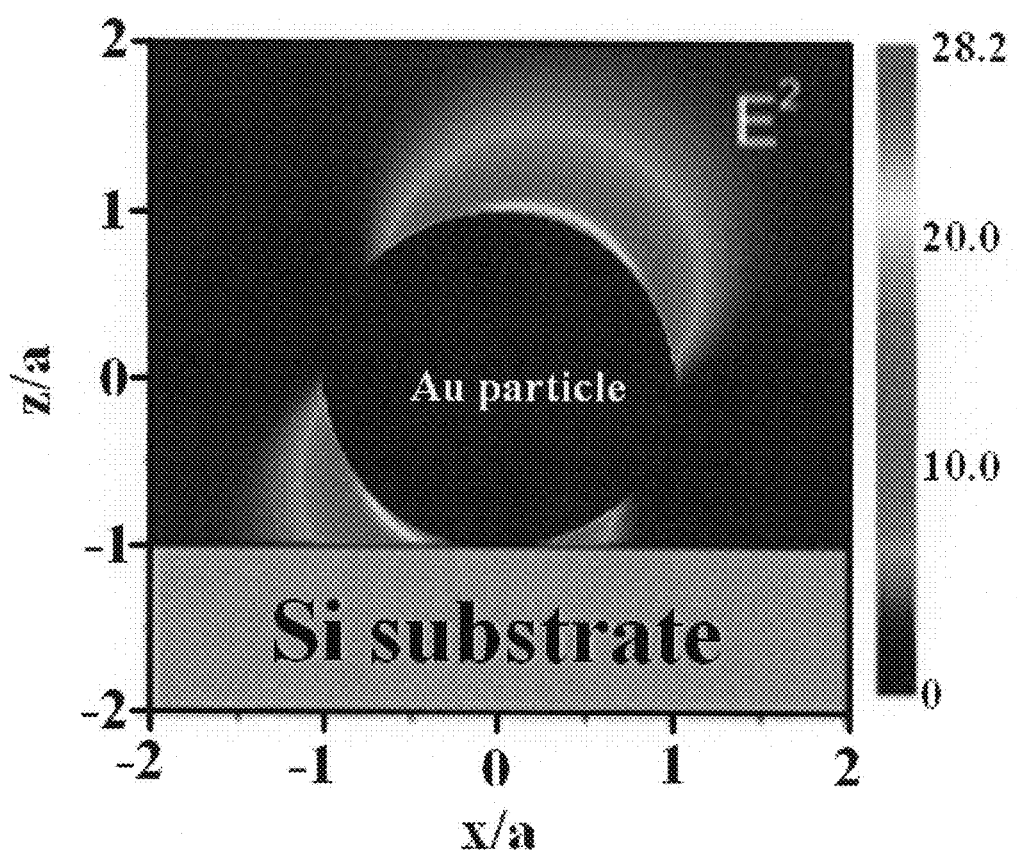
FIG. 4 illustrates a Mie simulation of the enhanced electromagnetic field around a 20 nm nanoparticle on a silicon substrate. (a) Intensity distribution side view, (b) intensity distribution top view, (c) field localization, and (d) Poynting vector distribution.

FIG. 4 illustrates the scattered field around a particle resting on a silicon interface. A single 40 nm diameter gold nanoparticle in a cytoplasmic solution resting on a thick silicon substrate was irradiated with 780 nm light at a 45° angle. Irradiating at a large angle ensures that the induced dipole will interact with the silicon substrate. Even when located on the silicon substrate, the nanoparticle exhibits pure dipole scattering with a maximum intensity enhancement of 26 at the gold-silicon interface. The FWHM of the dipole lobe interacting with the silicon substrate is 20 nm. The Poynting vector describes the direction of the energy flow during irradiation. For the 40 nm particle, Poynting vector is maximum along the particle-silicon boundary, having a value of 5.9, and also exhibits dipole properties.

Figure 5C:
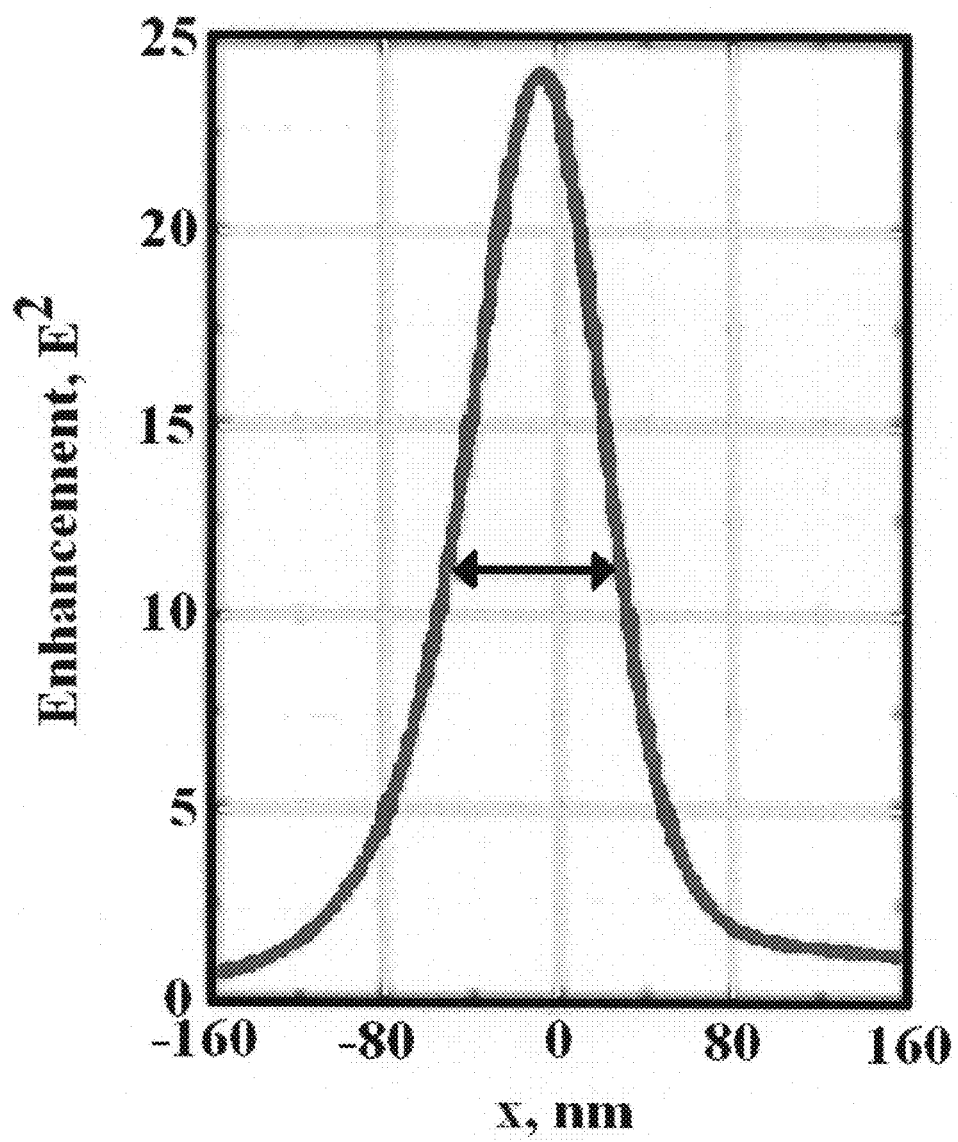
FIG. 5 illustrates a Mie simulation of the enhanced electromagnetic field around an 80 nm nanoparticle on a silicon substrate. (a) intensity distribution side view, (b) intensity distribution top view, (c) field localization, and (d) Poynting vector distribution.

FIG. 5 illustrates this local scattering effect for a 160 nm particle. Again, a single gold nanoparticle in a cytoplasmic solution resting on a thick silicon substrate was irradiated with 780 nm light at a 45° angle. The nanoparticle exhibits dipole scattering, but each lobe is offset from the true dipole plane such that there is a 120° angle between the two lobes. A maximum intensity enhancement of 24.2 was found along the particle-silicon interface. The FWHM of the dipole lobe interacting with the silicon substrate is 80 nm. The Poynting vector is maximum along the gold-silicon boundary, having a value of 9.3, and also exhibits properties of broadened quadrapole. Those most of the energy is concentrated along the particle-silicon interface.

In general, any material may be modified using the methods of the present invention so long as the material is at least partially solid. For example, the solid to be modified may be made in whole or in part from one or more of, but not limited to, silicon, glass, polymers, plastic, graphite, ceramic, metal, and Hafnium. The material may be biological such as, for example, bone (including teeth), cells, subcellular and extracellular sites, atherosclerotic plaques, blood clots, and connective tissues, tumors, and the like. Other suitable biological materials include, but are not limited to, cellular targeting regions, for example, membrane receptors (e.g., antibody, ligand, peptide mediated), subcellular organelles, RNA, DNA, chromatin, and proteins.

To facilitate a better understanding of the present invention, the following examples of specific embodiments are given. In no way should the following examples be read to limit or define the entire scope of the invention.

EXAMPLES

Example 1

Imaging and Ablation System

Figure 6:
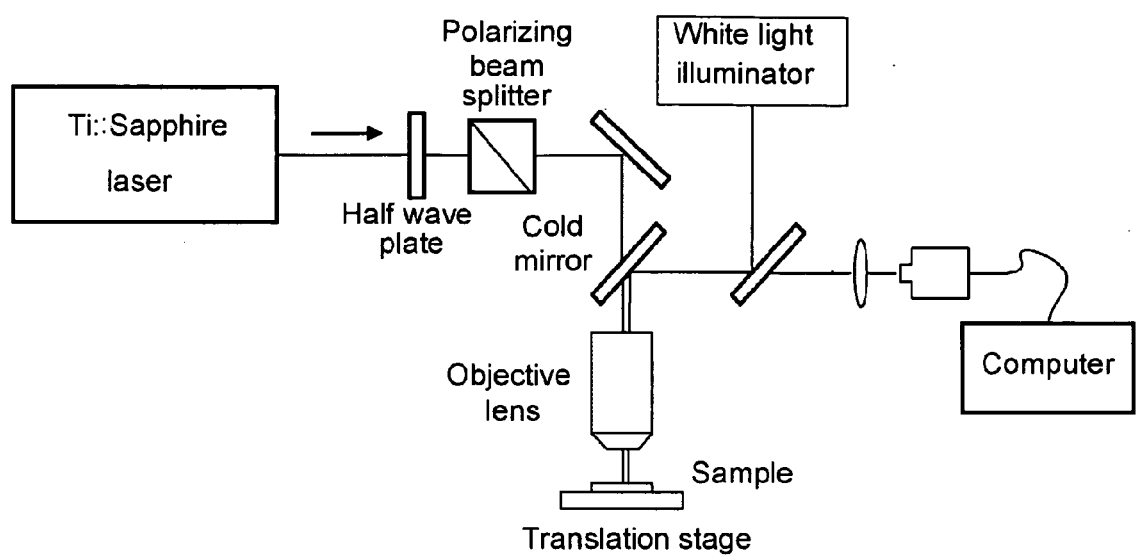
FIG. 6 illustrates a plasmonic femtosecond laser nanoablation system with epiluminescent imaging system.

Samples were irradiated and imaged using a lab-developed system, as shown in FIG. 6. An amplified femtosecond Ti:sapphire laser system (SpectraPhysics, MountainView, Calif.) delivers amplified single laser pulses of 220 fs temporal width at 780 nm wavelength at a 1 kHz repetition rate. An attenuator consisting of a half-wave plate and a polarizing cube beam-splitter was used to control the delivered laser power. Pulse energies were measured before the focusing system using an energy meter (Ophir PL10). The measured pulse energy transmission through the focusing system was estimated to be 64% by finding the ratio of energy before and after the objective. The sample was mounted onto an x-y translational stage. The setup provided simultaneous optical imaging and ablation of the sample through the same objective lens. A long working distance objective lens (0.28 NA, 10×; Mitutoya) was used to focus a linearly polarized laser pulse to a 1/e² radius of 3.2±0.2 μm at the beam waist. To obtain a homogeneous, well-defined energy distribution on the target, a circular aperture (6.5 mm in diameter) was placed in the beam path just before the objective. The spatial profile of the truncated beam, originally 8 mm in diameter, was not significantly modulated at the sample plane. All experiments were performed in air at atmospheric pressure. The orientation of the laser polarization at the sample plane was varied through the manipulation of the sample. When the laser light was directed orthogonal to the sample, the laser polarization was parallel to the substrate surface. For the laser to be directed at a 45° angle with respect to the silicon surface, the substrate was mounted onto a standard 45° angle Scanning Electron Microscope (SEM) block. By rotating the angled sample 90°, the electric field was either oriented into (p-polarized laser light) or along (s-polarized laser light) the surface plane. The size of the ellipticity of the irradiation zone was modulated as the sample was angled with respect to the laser. The axis of the beam that was aligned along the angled sample plane was lengthened by a factor √2.

Gold Nanosphere Production

Gold particles were produced according to the Turkevich method, in which particles were synthesized by the reduction of $HAuCl_4$ with sodium citrate. Atomic Force Microscopy (AFM; Dimension 3100 AFM, Digital Instruments) and Scanning Electron Microscopy (SEM; LEOS 1530) were used to measure particle dimensions. Two small diameter, near-spherical particle types of 80±5 nm and 50±5 nm (1.14 ellipticity) were developed in-house. Particle sizes above 100 nm were purchased from British Biocell International. AFM imaging was operated in tapping mode in air, using triangular shaped silicon cantilevers (40 N/m spring constant and 300 kHz resonance frequency; Budget Sensors). Nanoparticles were found to have negligible absorption properties at 780 nm, which was measured using spectrophotometry.

Preparation of Silicon

A silicon (100) wafer (bandgap energy of 1.14 eV) having a 21 Å native oxide layer as measured by ellipsometry was cut into a 5×5 mm piece and washed using a four step process: sulfuric acid, distilled water, acetone, and methanol. The wafer was ultrasonicated in each solution for 5 min and stored in methanol until use. A 6 μL aliquot of colloidal gold (2R=150 nm) was deposited onto the surface. The sample was annealed in air at 120° C. for 5 min. Using this method, isolated particles could be deposited on the substrate surface. Before and after irradiation, samples were characterized using SEM and AFM.

Preparation of Borosilicate Glass

A 1.1 mm thick borosilicate glass plate (Borofloat, <1 nm surface roughness; Precision Glass and Optics, Santa Ana, Calif.) was cut into 5×5 mm pieces and washed in methanol under sonication for 25 minutes. The chemical composition of borosilicate glass is 81% SiO2, 13% B2O2, 2% Al2O3, and 4% NaO2 and its band gap energy is about $E_b$~4 eV. A 6 microliter aliquot of colloidal gold (2R=80 nm) was deposited onto the surface and the sample was annealed in air at 120° C. for five minutes. By slowly heating the surface, we were able to obtain a broad distribution of particle arrangements on the surface ranging from single particles to micron-sized aggregates.

Preparation of Gold Bioconjugates

Anti-EGFR/Gold Bioconjugates were prepared using the 50 nm colloidal gold solution. Briefly, to prevent competitive binding of citrate ions with antibodies, 2 mL gold nanoparticles ($10^{12}$ particles/mL) were centrifuged at 2,000×G and resuspended in 2 mL 20 mM HEPES buffer (pH=7.47, Fisher Scientific). 2 μL of anti-EGFR monoclonal antibodies (clone 225, Sigma) were purified using 100 k MW centrifugal filter tubes (Centricon) and resuspended in 1.98 mL of 20 mM HEPES buffer. The gold solution is added dropwise to the dilute antibody solution, which is kept under constant stirring to allow for even coating of the nanoparticles, and allowed to interact for 45 minutes. 400 μL of 2% polyethyleneglycol (4 kDa MW; Sigma) was added to the mixture to prevent aggregation and the solution was centrifuged at 300×G for 45 min. The centrifugation process is necessary to remove unbound antibodies from the solution, which will competitively bind to EGFR during the labeling process. The bioconjugate pellet was resuspended in 300 μL phostphate buffered saline (PBS; Sigma) without $Ca^{2+}$ and $Mg^{2+}$ and stored at 4° C. until use.

Preparation of Cancer Cells

MDA-MB-468 epithelial breast cancer cells (American Type Culture Collection) were cultured in Dulbecco's modification of Eagle's medium (DMEM, Gibco) supplemented with 10% Fetal Bovine Serum (Sigma), 100 U ml$^{-1}$ penicillin (Sigma), and 100 μg ml$^{-1}$ streptomycin. The cells were maintained at 37° C. in a humidified 5% $CO_2$ atmosphere. Cells are cleaved from the flasks with a solution of 0.05% w/v trypsin (Sigma) and seeded, 3.7×10⁵ cells onto glass well Petri dishes (MaTek) treated with fibronectin and irradiated 14 hr later. Before laser exposure, cells were washed (3×2 mL DPBS) and incubated in 100 μL of gold bioconjugate solution for 20 min at 37° C. After nanoparticle incubation, cells were washed (3×2 mL DPBS) to remove unbound bioconjugates from the solution and resuspended in 2 mL DPBS. Cells were immediately used in phototherapy experiments to minimize nanoparticle endocytosis. FIG. 14 provides a dark field and multiphoton image of MDA-MB-468 cells labeled with anti-EGFR gold bioconjugates.

Ablation of Silicon (100)

We demonstrate the fabrication of nanostructures ablated on silicon (100) by the plasmonic scattering of 780 nm, 220 fs laser pulses in the near-field of gold nanospheres. Gold nanospheres of 150 nm diameter were deposited onto a silicon surface and irradiated with a single laser pulse. We studied the effect of laser polarization on the morphology of ablated nanostructures and estimated the minimum fluence for plasmonic nanoablation.

Single Laser Pulse Ablation Properties of Crystalline Silicon

Silicon is a material having a low overall femtosecond laser ablation threshold similar to one for metal materials such as gold. A common method for estimating the single-shot ablation threshold of silicon (100) $F_{abl,th}$ is through the linear relationship between the ablation depth $h_a$ and the average fluence $F_0^{ave}$:

$$h_a = \alpha_{eff}^{-1} \ln\left(\frac{F_0^{ave}}{F_{abl,th}}\right), \qquad (2)$$

where $\alpha_{eff}^{-1}$ is the effective optical penetration depth and $F_{abl,th}$ is the pulse fluence when $h_a$=0. Ablation depth data measured using AFM was plotted with respect to the corresponding laser fluences. Extrapolating the linear fit to zero, we find the single-shot ablation threshold of silicon to be $F_{abl,th}$=191±14 mJ/cm². Uncertainty in the ablation threshold measurement arises mainly due to the error in the measured spot size and pulse-to-pulse energy variability.

Ablation craters generated at laser fluences lower than about 1 J/cm² are mediated by the optical penetration depth.

At 780 nm wavelength, the dominant mechanism of electron excitation is single photon absorption due to the photon energy (1.6 eV) having greater energy than the silicon bandgap (1.14 eV). Since absorption is linear, the ablation profile will resemble the intensity distribution of the incident light. As the laser fluence is increased above 1 J/cm², thermal effects begin to affect the surrounding lattice. Carrier conduction contributions become important and the electron-driven heat penetration depth defines the ablation depth.

Before the onset of true ablation, i.e. removal of material, irradiation of silicon with a low fluence laser pulse can result in surface modification. Below the ablation threshold the molten layer will resolidify either into an amorphous or re-crystallized state. The amorphous region marks the lowest input energy needed to achieve modification. The molten layer re-solidifies faster than the re-crystallization time scale, leaving it in an amorphous state. The single shot modification threshold for silicon (100) was estimated to be about 186 mJ/cm².

Effect of Gold Nanoparticles on Silicon Ablation

Figure 8A:
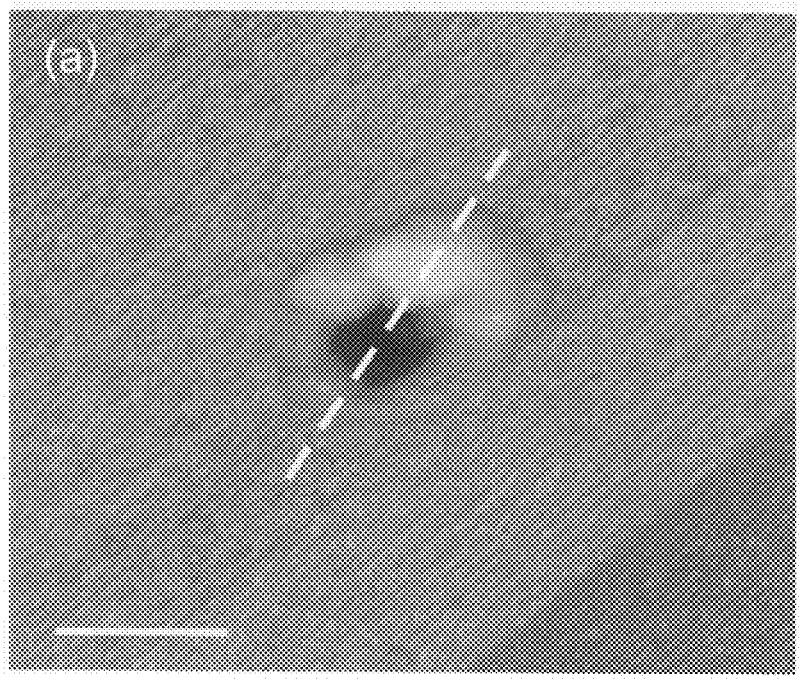
Figure 8B:
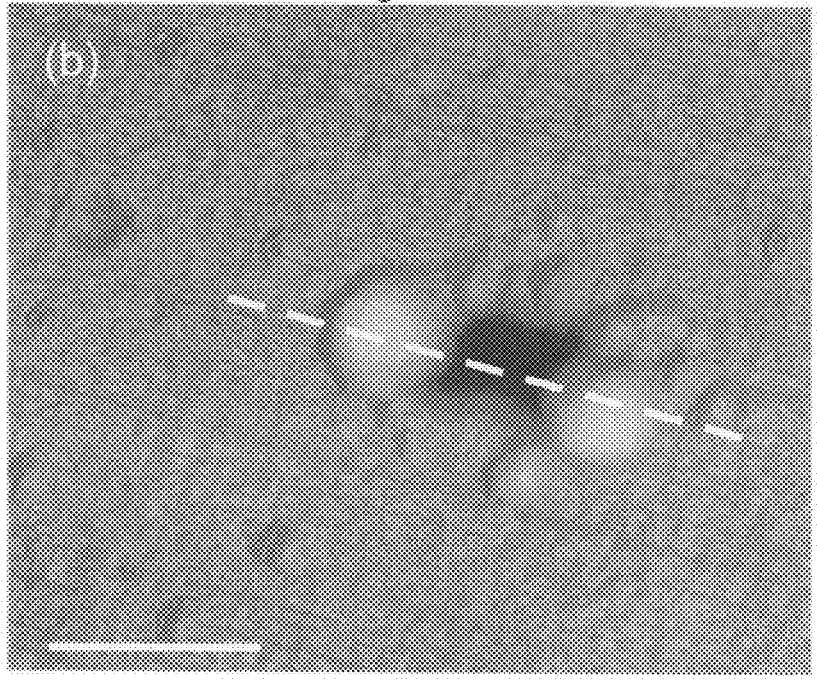
Figure 8C:
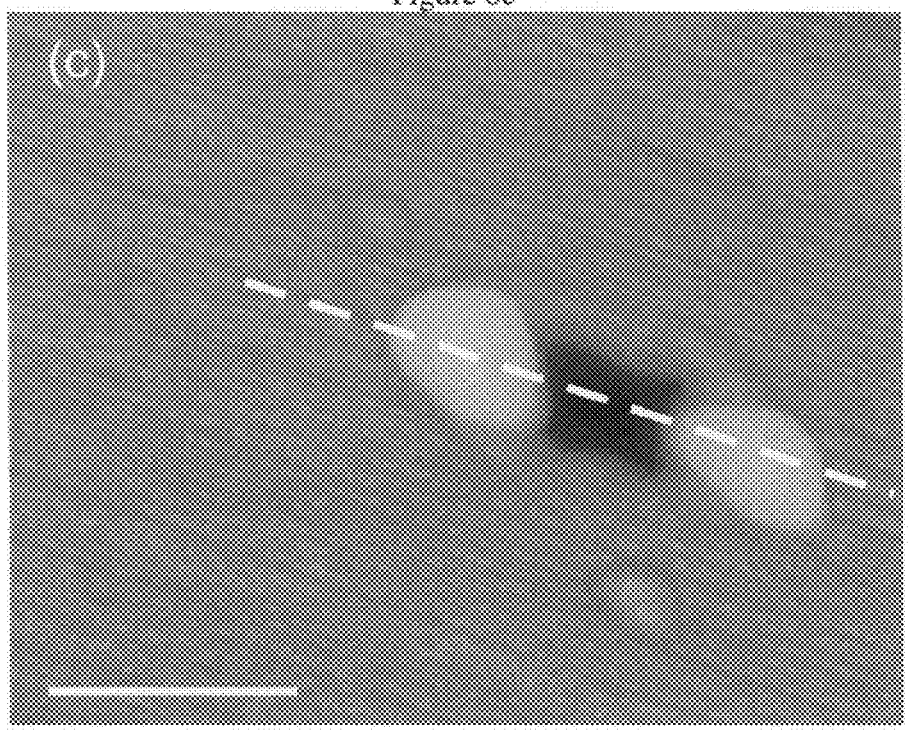
Figure 8D:
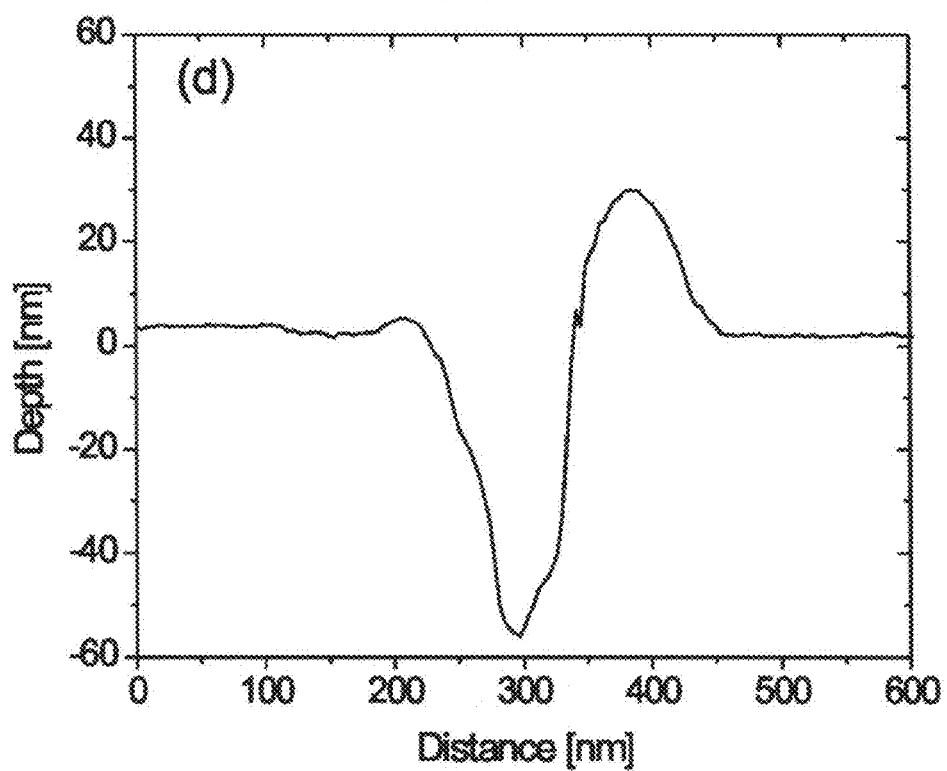
Figure 8E:
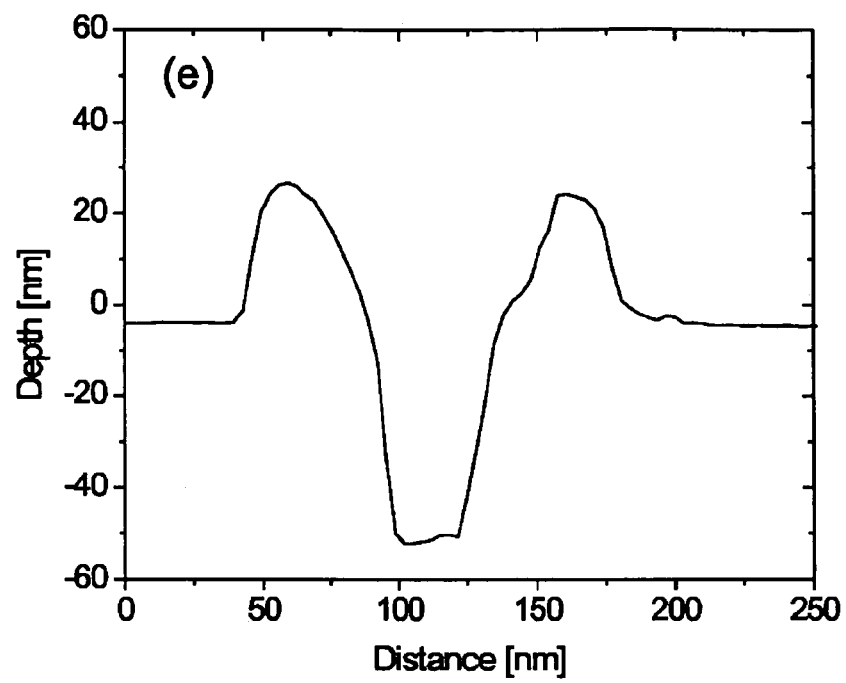
Figure 8F:
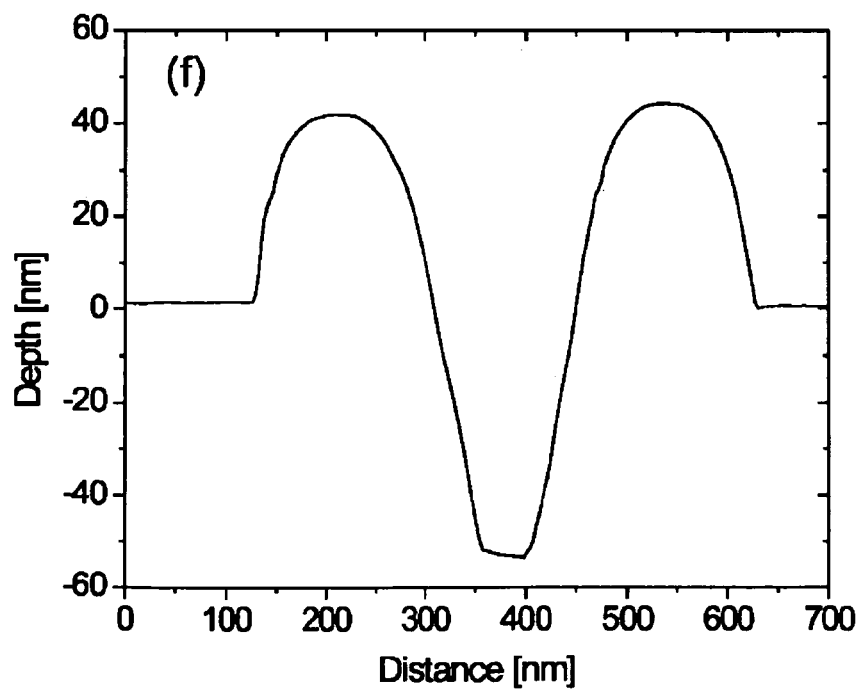

FIG. 7 shows an SEM image of a nanoparticle studded silicon (100) wafer after irradiation by an elliptically shaped laser pulse of 190 mJ/cm² average fluence. In FIG. 8(b), a Gaussian curve representing the peak incident fluence along the short axis is given as a reference to the different ablation regimes along the irradiation zone. The spatial profile of a Gaussian beam is given by $$F(r) = F_0^{peak} \exp\left(-\frac{2r^2}{w_0^2}\right), \quad (3)$$

where $F_0^{peak}$ is the laser peak fluence and r is the distance from the center of the beam. Typically the fluence is given in terms of an average value instead of the peak fluence. The average fluence can be determined by:

$$F_0^{ave} = \frac{E_{pulse}}{\pi w_0^2}. \quad (4)$$

The incident pulse was directed such that it was orthogonal to the substrate surface with the E-field along the short axis of the elliptical pulse. The application of a laser pulse having a Gaussian intensity distribution allows for a broad range of laser fluences to be studied in a single experiment. A few identifiable regions of surface modification are observable. In increasing distance from irradiation center these regions are:

1. Amorphization of Si (100): In the center, there is a region of surface modification due to the amorphization of Si (100). In this region, no material is removed from the substrate, which is confirmed with AFM. The surface roughness, however, increases to about 5 nm. Amorphization occurs until the laser fluence drops to approximately 176 mJ/cm², which agrees with the modification threshold stated earlier. All particles in this region are completely ablated and any plasmonic effect is washed out due to long silicon melt times.

2. Ablation induced by local enhancement near the particles: Here a region of surface ablation is observed on the micron-scale, induced by the laser enhancement in the near-field of the particles. The ablation craters are surrounded by a region of surface melt. Generally, rim structures and splash zones border the melt zones. Again, particles are completely ablated at this laser fluence level.

3. Ablation at the nano-scale via local enhancement near the particles: The enhancement in the vicinity of the particles generates nanoscale craters on the silicon surface that are direct imprints of the dipolar scattering pattern with any surrounding damage to the silicon lattice. Here the laser fluence is not large enough to completely ablate the particle. The collective oscillations of electrons (surface plasmons) in the nanoparticle cause the particle to split into two halves. The molten gold generally resolidifies at the outer edges of the ablation crater. In the case of plasmonic ablation for nanolithography applications, it would be ideal to work in this fluence level. Material removal only extends tens of nanometers from the particle center and is confined to the nanoscale.

4. No surface modification/ablation: The incident laser fluence continues to decrease such that the local enhancement generated by the particle is not enough to overcome the modification threshold of the silicon substrate. As will be described later, this ablation limit occurs at an average fluence of 27.5 mJ/cm² when the laser polarization is oriented parallel to the silicon surface. Beyond this point, both silicon and gold remain intact.

Ablation Threshold for Gold Nanospheres

The gold nanoparticle ablation threshold between 20 to 25 mJ/cm² was determined, which was defined as the laser fluence below which the whole spherical structure of the particle remains intact. This value is in good agreement with the recently reported damage threshold value of 15.5 mJ/cm² for nanospheres of 38 nm in diameter irradiated by 400 nm, 100 fs laser pulses. In those studies, picosecond x-ray scattering measurements revealed that partial material removal from the poles of the nanoparticle occurs for fluences above 15.5 mJ/cm². Below 20-25 mJ/cm², some material removal may be expected to occur, reducing the overall size of the particle in regions of intense scattering. In cases where the plasmonic ablation threshold of silicon is lower than the ablation threshold of the gold particle, nanocrater structures may form underneath the particle itself for fluences down to the threshold value.

Effects of Laser Polarization on Nanocrater Morphology

We studied the effect of laser polarization on the morphology of ablated nanostructures. FIG. 8 presents AFM images and cross-sectional profiles of three nanocraters obtained using different cases of laser polarizations. In each case, the scattering pattern in the particle near-field was directly imprinted into the silicon surface. When the incident radiation E-field is directed at a 45° angle into the silicon substrate surface (p-polarized laser light), only one lobe of the dipolar scattering region interacts with the underlying substrate, leading to the formation of a single circular crater. In FIG. 8(a), the relative fluence interacting with the particle was 88 mJ/cm². A crater having 100 nm diameter and 53 nm maximum depth was generated. Images of craters produced by laser polarizations parallel to the substrate surface when the substrate is angled 0° and 45° to the incident irradiation are shown in FIGS. 8(b-c), respectively. In each of the cases when the laser polarization is parallel to the substrate surface, the generated craters have a double-lobed crater structure, which follows the dipolar scattering pattern of the nanoparticle. Resolidified gold is found at the ends of each dipolar crater structure after ablation. In FIG. 9, the gold can be clearly visualized and is represented as the peak(s) surrounding the craters in the cross-sectional profiles.

Plasmonic Laser Nanoablation Threshold

For each polarization orientation, the minimum threshold fluence for plasmonic nanoablation was measured. As shown in FIG. 9, the maximum depth of generated nanocraters for a broad range of laser fluences is measured using AFM and plotted against the average fluence that interacted with the particle at that point. Determination of the relative fluence at the point of particle ablation is nontrivial in those cases where sample irradiation was at an angle. Each nanocrater rests on a distinct plane some distance above the beam waist, which can be determined according to its location on the substrate. Since the sample is located at a distance above the Rayleigh range, the spot size interacting at the sample plane will change according to height. Each distinct plane will have a unique spot size that can be found using Equation 1. Determination of the relative fluence at the nanocrater location results from projecting each nanocrater onto its corresponding ablation plane. A linear fit to data points follows the relationship given in Equation 3. Extrapolation of the linear fit line to zero provides the "enhanced single-shot ablation threshold." For p-polarized laser light at 45°, the required fluence for surface ablation is reduced to 8.2±2.9 mJ/cm². Ablation thresholds determined for laser polarizations parallel to the substrate surface when the substrate is angled 0 and 45° (s-polarized laser light) to the incident irradiation are 27.5±4.3 mJ/cm² and 46.7±16.3 mJ/cm² respectively. The errors were estimated based on the covariance of the data with respect to the linear fit. In Eq. 3, both $\alpha_{eff}^{-1}$ and $\alpha_{eff}^{-1} \ln(F_{th,abl})$ have an associated error. From these errors, we can calculate a set of linear fits that will provide a range of possible ablation thresholds.

The near-field enhancement factor is a measure of the particle's ability to efficiently collect light from a cross-section larger than its geometrical cross-section and scatter it into a nanoscale region necessary for material ablation. Nedyalkov et al. previously determined the near-field enhancement factor by finding the ratio of the lasers fluences required to achieve the same ablation depth with and without nanoparticles present on the substrate. The use of the "standard single-shot ablation threshold" as found from $h_a$ measurements is proposed herein for estimating the nanoparticle near-field enhancement factor. The experimental near-field enhancement factor is estimated using the relationship:

$$\gamma_{eff} = F_{th}/F_{th}^{np}$$

For the p-polarized irradiation of a particle at a 45° angle, the relationship gives an experimental near-field enhancement of $\gamma_{eff}$=23.1±7.6. Normal incidence and s-polarized light at 45° gives enhancements of $\gamma_{eff}$=6.9±0.6 and $\gamma_{eff}$=4.1±1.3, respectively.

Theoretical Simulation of Laser Interaction

To validate these measurements, we calculated the near-field intensity based on the solution of the boundary-value problem for a spherical particle on a flat semi-infinite substrate. It is assumed that an incident plane wave with 780 nm wavelength propagates along the z-coordinate. The angle of irradiation and direction of the electric field are varied according to polarization type. The particle is 150 nm in diameter. Additional multi-reflections between the particle and the substrate, which can lead to further intensity variation along the surface, are taken into account. For a transparent particle on the substrate irradiated with normal incidence, the intensity absorbed by the substrate can be estimated by is the following relationship:

$$I \approx \frac{I_0(1-R)}{1-b \cdot R}, \quad (5)$$

where $I_0$ is the Mie intensity around the particle when its not resting on a substrate, R is the substrate reflectivity, and b is the back-scattering efficiency of the particle. When b<1, the intensity will be smaller and for b>1, the intensity will be higher than the Mie intensity. The native oxide layer was ignored because of its negligible effect on the substrate refractive indices.

Two sets of calculations were performed to determine the effect of the incident pulse energy absorption by the silicon.

1. Initial experiments are completed with the silicon at room temperature, having optical constants n=3.930 and κ=0.136. In this case, the silicon surface does not interact with the incident pulse and the field enhancement around the particle was due solely to the interaction of the laser pulse with the particle. The optical constants of the 150 nm gold particle are calculated using the Drude free electron model, giving n=0.195 and κ=4.910.

2. In the second case, the formation of a low-density plasma along the silicon surface was assumed. Here the silicon interacts with the incident pulse by absorbing some of the incident pulse energy. It was assumed that a steady-state plasma was formed at the exact onset of the pulse. Experimentally this will not be the case, for free electrons will be generated continually over the pulse duration, increasing the surface absorptivity and reflectivity with time. For this general case, optical constants for silicon were given as n=4.0 and κ=4.5.

FIG. 10 shows the calculated field intensity, i.e. the Poynting Vector, along the substrate surface for both cases. First, with respect to the theoretical enhancement for irradiation with p-polarized light angled at 45°, an enhancement of 17.2 is found for the first case and 23.9 for the second case. This shows that the absorption of the incident energy by the silicon has a large effect on the near-field enhancement of the particle. For simplicity in the calculation, the formation of a steady-state plasma was assumed, but in reality a plasma with time-dependent density will form during the pulse duration. This agrees with the found experimental results, where the measured field enhancement is between the two theoretical values. As the silicon absorbs the incident energy over the pulse duration, the absorptivity and reflectivity of the silicon will continue to increase, generating larger enhancements in the particle vicinity.

For normal incidence and the s-polarization cases, larger experimental values are found than those presented theoretically. A number of factors could be contributing to the increased enhancement. A large part of the extra enhancement contributed to the experimental results for normal incidence is believe to be due to increased surface reflectivity, causing a larger number of reflections from the silicon surface to interact with the particle. The reflected waves off the surface will directly interact with the particle. In the s-polarized at 45° irradiation case, most of the wave is reflected at an angle away from the particle. Only a small part of the reflected wave interacts with the particle. A slight increase in enhancement beyond the theoretically calculated value is seen. Other factors could include other nonlinear effects due to the ultrashort laser pulses or ultrasmall confinement of light or phase changes in the gold particle during irradiation.

Ablation of Borosilicate Glass

Borosilicate glass is a dielectric material that exhibits similar femtosecond laser ablation properties as that of biological materials, making it a model substrate to study the plasmonic ablation of tissue in a controlled environment. We studded a borosilicate glass surface with a broad distribution of particle arrangements ranging from single 80 nm particles to micron-sized aggregates. Three effects were studied: (1) minimum threshold fluence necessary for plasmonic nanoablation in the single- and multi-particle cases; (2) effect of cluster orientation with respect to laser polarization on minimum threshold and crater morphology; (3) effect of cluster size and geometry on minimum threshold.

Single Laser Pulse Ablation Properties of Borosilicate Glass

Transparent materials do not absorb radiation from the visible to near-infrared portions of the electromagnetic spectrum. As is such, optical breakdown in transparent materials requires incident fields of high peak intensities exceeding $10^{11}$ W/cm$^2$. Tightly focused femtosecond laser pulses provide the necessary intensities to initiate nonlinear absorption processes of the incident laser energy. Large numbers of electrons in the medium are excited by the high flux of photons, since the electrostatic force felt by the valence electrons becomes large enough to excite the bound electrons out of the Coulomb potential. A sufficiently high electron density plasma results and material vaporization occurs. The laser-induced plasma absorbs photon energy via nonlinear ionization mechanisms and ablation, i.e. material ejection, occurs when the density of free conduction band electrons reaches a critical density. The minimum fluence necessary to initiate ablation is called the optical breakdown threshold and materials experience permanent modification.

Since femtosecond pulses are of high intensity, optical breakdown is intrinsically different from that of longer pulse ablation. Seed free electrons are generated independent of the initial electron concentration in the material. This is not true when ablating materials with pulses greater than 10 ps, where material impurities provide the source for seed electrons. Also, since the pulse duration is shorter than the material heat conduction time, electrons are unable to transfer absorbed energy to the surrounding lattice, thus there is no change in the electron-lattice dynamics during the ablation process. Only the intense heating and rapid expansion of material at the focal volume account for the vaporization of the bulk material.

We found the single-shot ablation threshold of borosilicate glass in air to be $F_{abl,th}=1.88\pm0.08$ J/cm$^2$, which agrees well with literature. This threshold was determined exactly as was presented with the silicon data.

Effect of Gold Nanoparticles on Borosilicate Glass Ablation

After ablation by a single, 780 nm, 220 fs laser pulse, the surface of the borosilicate glass only exhibits one type of surface ablation; all ablations were on the nanoscale. Since dielectric ablation by femtosecond pulses is plasma mediated rather than generated through rapid heat deposition, no micron-sized ablation craters will be found at higher fluences. In the ablation of Si (100), this was not the case; at high fluences, thermal effects begin to affect the surrounding lattice, generating dipolar craters surrounded by a region of surface melt and splash zones. The gold nanoparticle ablation threshold of 20 to 25 mJ/cm$^2$, which we define as the laser fluence below which the whole spherical structure of the particle remains intact, was again verified in the glass experiments.

Nanoablation by Single Particles

FIG. 11 shows a three-dimensional AFM scan of an ablation crater by a single particle irradiated with a relative fluence of 1.2 J/cm$^2$. The crater has a double-lobed structure, which follows the dipolar scattering pattern of the nanoparticle. Crater dimensions are 30 nm depth and 271 nm length. No residual gold was found in the crater vicinity. Since the femtosecond laser ablation threshold of dielectrics is approximately an order of magnitude higher than that of gold, the gold nanoparticle will vaporize at each nanoablation site.

To determine the minimum threshold necessary for plasmonic nanoablation, the maximum depth of generated nanocraters is measured using atomic force microscopy and plotted against the relative fluence that interacted with the particle at that point. FIG. 12 again illustrates that the data fit shows a linear between the crater depth and the logarithm of laser fluence. As with silicon nanoablation, extrapolation of the linear fit line to zero provides the "enhanced single-shot ablation threshold". Using this technique, we find a single particle threshold fluence of 226.8 mJ/cm$^2$, which correlates to an optical enhancement of 7.4.

Using the same theoretical model as presented in the silicon data, we found a theoretical enhancement for an 80 nm, gold nanosphere resting on a semi-infinite dielectric substrate irradiated by 780 nm laser light. The simulation was run without the formation of a low-density plasma during irradiation. The Poynting vector along the substrate surface indicates an enhancement of 1.67. This value, as in silicon experiments, is lower than the found experimental enhancement. Again, it is reasonable to assume the formation of a time-dependent low-density plasma during irradiation which increase the degree of enhancement.

Nanoablation by Particle Clusters

Crater morphology and the single shot ablation threshold depend upon aggregate size, geometry, and orientation to the laser polarization. Since much of the scattered waves are confined within an aggregate, generated craters are direct imprints of the aggregate size and geometry. Crater profiles exhibit nanoarchitecture describing the location of the individual particles in the cluster. As with single particles, it is again feasible to elucidate the aggregate ablation threshold via the linear relationship between the single-shot ablation depth and the logarithm of the relative laser fluence. However, the relationship is only valid when comparing craters generated by particle aggregates of the same number of particles and geometry, in addition to the same orientation to the laser polarization. This has been verified experimentally and can be described theoretically using the dipole-dipole interaction model The minimum fluence necessary for ablation by two- and three-particle aggregates oriented at a 45° angle to the laser polarization has been studied. The two-particle aggregate ablation threshold is 132 mJ/cm$^2$, yielding a near-field enhancement of 12.2. We find a threshold of 52 mJ/cm$^2$ for the three-particle aggregate, yielding a near-field enhancement of 28.8. FIG. 13 compares the ablation threshold values for the single-, two-, and three-particle aggregate cases two particle, and three particle clusters. As is evident, the ablation threshold decreases with an increasing number of particles found within an aggregate. The increased enhancement is a direct result of the constructive interference of all the individually scattered fields within the cluster. This generates "hotspots," regions of strong scattered wave interaction, of which the location depends upon the aggregate orientation to the laser polarization.

The enhanced single-shot ablation threshold relationship is valid only for particle aggregates having the same geometry and orientation with respect to the laser polarization. To verify this, lets look at a brief experimental example. We make the statement that the ablation process is highly dependant on the laser polarization direction. Lets observe two independent three particle clusters irradiated with a relative fluence of 0.47 J/cm$^2$, where one cluster is oriented in the direction of the polarization and the other is at a 45° angle to the laser polarization. The cluster positioned along the polarization direction has a depth of 10.3 nm, while the other cluster has a depth of 2.5 nm. It can be concluded that the cluster positioned along the direction of polarization will have a greater enhancement, leading to a lower ablation threshold value.

The interaction of closely spaced particles, i.e., particle coupling, has a strong effect on the location and width of the plasmon resonance. For a simple understanding of particle coupling, the dipole-dipole interaction model is used to describe the plasmonic interaction of two closely spaced nanospheres. As was previously described, the surface plasmon response is confined along the particle surface. When certain conditions are met, the system becomes resonant and the particle strongly interacts with the incident light. Now, a second particle is placed within the oscillating field of the first particle. Upon polarization of the conduction electrons by the incident field, additional forces act upon both particles. First, let us observe a particle pair oriented such that the long axis is orthogonal to the incident electric field. In this case, the repulsive force of the surface charges is enhanced, leading to a higher resonance frequency and effectively blue shifting the plasmon resonance to lower wavelengths. The opposite effect occurs when the electric field is parallel to the long axis of the particle pair. In this case, the plasmon band shifts and stronger enhancement will be seen in the near-infrared. As a quick note, particle interaction has been seen out to separation lengths of 5 particle diameters.

The near-field scattering is greatly affected by particle aggregation. With particle aggregation, the near-field enhancement becomes a function of all the individually scattered wavelets from particles in the aggregate. Essentially, primary particles in the aggregate electromagnetically couple, exhibiting additional extinction features at longer wavelengths $\lambda$, where the surface plasmon is strongly decreased in single particle irradiation. At longer wavelengths, scattering processes dominate the plasmon band, where absorption still dominates in shorter wavelengths, but will again be negligible in the NIR regime. Because the superposition of scattered waves is responsible for the near-field enhancement, aggregate size will have a finite limit, beyond which the maximal optical enhancement saturates. This limit will depend upon particle cross-talk and deconstructive interference effects.

MDA-MB-468 Cell Study

Borosilicate glass experiments show that nanoparticle clusters are extremely important when considering plasmonic nanosurgery in cells. The constructive interference of all the scattered waves significantly increases the overall enhancement of the cluster. Dark-field and multi-photon luminescence images in FIG. 14 show that the nanoparticles across the cell surface are randomly distributed forming various sizes of clusters. Rather, the particles dot the surface randomly and the distribution ranges from single particles to micron sized clusters. Furthermore, the receptors to which the nanoparticles are attached are not stationary, rather they are fluid and move with great ease across the surface. This uneven distribution across the surface is advantageous when considering plasmonic laser nanosurgery. The clusters will create large localized enhancements at the cell plasma membrane. The generation of nanosized plasmas will create pores in the bilipid layer effectively killing the cell.

Single Shot Cellular Membrane Photodisruption

Both labeled and unlabeled MDA-MB-468 cells were irradiated with single femtosecond laser pulses of 40 μm diameter. The fluence was varied from 40 mJ/cm$^2$ to 1.5 J/cm$^2$ to determine the cell death threshold for both labeled and unlabeled cells. Preliminary images were taken to show the cellular detail before irradiation. 5 minutes after irradiation, an image of the cell was again obtained. The cells were incubated at 37° C. for 1 hour after irradiation to ensure the cell fully concludes the death process. To confirm cell death, a 2 μM solution of Calcein AM (Sigma-Aldrich) was added to the cells. After a 1 hour interaction time, cells were imaged using an epifluorescence microscope. Unlabeled cells had a cell death threshold value of approximately 375 mJ/cm$^2$. The threshold level was reduced 7-8 times in the labeled cells to approximately 50 mJ/cm$^2$. FIG. 15 presents a standard epiluminescence image of cells killed by the corresponding threshold fluences. Dotted white circles mark regions of irradiation. Only cells in the irradiation zone were affected, showing that the extent of interaction is highly localized.

80 MHz Repetition Rate Cellular Membrane Photodisruption

MDA-MB-469 epithelial breast cancer cells immersed in a buffered saline medium were labeled with 50 nm gold nanospheres functionalized with Anti-EGFR at a concentration of 10$^5$ particles per cell. Approximately 20 cells per experiment were imaged as a series of 32 images, each 1 μm apart through the depth of the cell layer at a laser power of 180 μW. To ensure membrane integrity, the cells were immersed in a fluorescent probe fluorescein isothiocyanate-conjugated dextrane (50 μL, 10 kDa FITC-Dextran, 25 mg ml$^{-1}$; Sigma). The dye is impermeable to live cells with intact membranes, as is shown in FIG. 16(*a*). Onto the center plane of the cell layer, 1.5 mW laser light (760 nm, 80 MHz) was scanned for 10 sec, during which the cells were scanned approximately 7 times. In each scan cycle, individual pixels were exposed for 2.5 μs, corresponding to the application of 200 overlapping pulses per pixel. Poration (i.e. loss of membrane integrity), as shown in FIG. 16(*b*), was confirmed by the influx of the fluorescing dye into the cytosol.

To prove that photodisruption of the plasma membrane is due to the near-field enhancement effect instead of heating, we calculated heating properties of the 50 nm gold particles, as shown in FIG. 17. For these calculations, the particle optical and heating properties were modeled using Mie Theory and a two-temperature heat transfer model with surface conductance, respectively. At 760 nm wavelength, the particle is approximately 370 times more efficient in scattering light in the near-field than in absorbing incident energy, which has efficiency slightly less than 5% of the particle geometrical cross-section. Applying the absorption cross-section to the heating model, we find that the maximum water and particle temperatures in a single pulse are 8K and 3K, respectively. To understand the cumulative heating effects, we also studied multiple-pulse heating at 80 MHz. At the end of each pulse (12.5 ns), the temperature drops significantly to near-negligible heating effects. Over 80 pulses, water temperature reaches only 1K, which is not enough to induce thermal damage to the cells.

If the photodisruption is a near-field enhancement effect, the peak laser intensity in the particle near-field must be understood. Experimentally, a near-field enhancement of 35 (the ratio between the average powers needed to photodisrupt labeled and unlabeled cells) is found, which corresponds to a laser intensity of 0.2×10$^{12}$ W/cm$^2$ in the particle near-field.

This value corresponds to the intensity necessary to create free-electrons in water to induce photochemical damage. In addition, field emission from the nanoparticle surface generated by the large enhancement as measure by Plech et al. may be contributing more free-electrons to the low density plasma causing cellular photodamage.

Conclusions

Nano-ablation was shown in three materials (silicon, borosilicate glass, and MDA-MB-468 cells) and corresponding threshold values correlated remarkably well with theoretical calculations.

To model ablation processes of dielectric materials in a controlled environment, nanoparticles were deposited onto borosilicate glass. From these studies, four very important conclusions can be drawn: (i) Crater depth and size is dependent on laser fluence; (ii) Clusters more effectively enhance the plasmonic scattering of light than single particles; (iii) Pit depth is not dependent on cluster size, but rather cluster shape and orientation to the laser polarization: (a) Those cluster "in line" with laser polarization produce larger enhancement, (b) Clusters having a very organized structure, i.e. rod, produce larger enhancement; and (iv) There is an upper limit in the cluster size, for plasmonic laser ablation to be effective. When this limit is reached, destructive interference begins to become more prevalent.

Using the linear relationship between the pit depth and the logarithm of the laser fluence, ablation thresholds were determined for single particles and clusters. Constructive interference of scattered waves in clusters generated larger enhancements, significantly lowering ablation thresholds compared to single particles. The orientation of the clusters to the laser polarization and their shape also significantly effected plasmonic enhancement. With more organized shapes, i.e. rods, plasmonic enhancement was enhanced. Through this analysis, it can be shown that a three particle cluster aligned in a rod shape will produce greater enhancement that a four particle cluster in a spherical arrangement. If this rod shape is aligned along the direction of the polarization, a further enhancement will be seen. This process was explained utilizing the dipole-dipole interaction model. Though, as cluster sizes increases, a saturation point is reached and deconstructive interference becomes more prevalent. This is generally seen in clusters greater than ten particles.

The cluster effect was greatly utilized in the cell study. It was shown that even with a "light" labeling of the cell, i.e. 100-500 particles, the cell death threshold is significantly reduced. This is possible due to the inhomogeneous distribution of EGF receptors on the cell surface, creating clusters. Since it is desirable to make PLN a cellular technique, these initial results were compared against other photoselective methods utilizing nanoparticle heating, which is shown in Table 1.

TABLE 1

| Group | Wavelength (nm) | Pulse Duration | Total Energy Deposition |
| --- | --- | --- | --- |
| Halas | 880 | CW | ~10,000 x |
| Lin | 532 | 20 ns | ~1,000 x |
| Huttman | 527 | 35 ps | ~800 x |
| Ben-Yakar | 780 | 100 fs | 1 x |

For 30 nm gold nanoparticles irradiated with wavelengths near their plasmon resonance, the total deposited energy varied from 7,200 to 800 times more depending upon pulse width. The shorter the pulse width, the lower the fluence required due to greater amounts of energy being deposited into the particle over shorter time scales. In addition, the technique fares extremely well versus other engineered nanostructures. Spherical nanoshell composite particles require 10,000 times more total fluence and gold nanorods require 3,600 times more fluence.

In addition, the use of small particles and near-infrared light allows for use of the technique deep within a tissue structure. Near-infrared light is not known to drive any natural photo-chemical processes. Thus any occurred processes are solely generated by the aforementioned technique.

Example 2

Purified SWCNTs manufactured by the high pressure CO process were provided by Carbon Nanotechnologies Incorporated (Houston, Tex.) with less than 15% ash content by weight. The as-received SWCNTs were further purified using modified oxidation and ultrasonication processes. Specifically, SWCNTs were oxidized in a box furnace for 14 hours at 275° C., followed by reflux in 2.5 M $HNO_3$ for 36 hours. The resulting mixture was filtered through a 100 nm pore size polycarbonate filter, rinsed, and re-suspended in N,N-dimethylmethanamide (DMF). Ultrasonication of the SWCNT/DMF mixture at a concentration of 50 mg/L for 2 hours was performed to cut the SWCNTs into shorter length. Centrifugation (5000 rpm, 45 mins) was used to remove larger unreacted impurities from the solution. Transmission Electron Microscope (TEM) image in FIG. 18 shows that the SWCNTs remain in a bundled state due to the substantial van der Waals attraction (~950 meV/nm). The diameter of the bundles varies between 5-25 nm. A 2 µL aqueous sample of SWCNT suspension was deposited onto a glass wafer, which was subsequently heated to 120° C. for 20 minutes on a hot plate to evaporate the DMF. Consequently, only a single layer of randomly distributed SWCNTs was left on the wafer. The density of SWCNTs on the glass wafer could be adjusted by the amount of solution deposited. Borosilicate glass wafers were used with surface roughness less than 1 nm from Precision Glass and Optics (Santa Ana, Calif.). The wafers were ultrasonically cleaned with methanol prior to use.

The experimental setup is schematically illustrated in FIG. 6.

To determine the laser ablation threshold of SWCNTs, the minimum local laser fluence were measured where SWCNTs started to disappear. Based on Gaussian spatial profile of the laser beam with a $1/e^2$ laser beam radius $w_0$, the radial distribution of laser fluence is presented above in Equation 3. For measured radius of disappearance of SWCNTs $r_0$, the local laser fluence is given by $$F_{th}(r_0) = 2F_{th}^a(r_0) = \frac{2E}{\pi w_0^2}\exp\left(-\frac{2r_0^2}{w_0^2}\right), \quad (6)$$

where $F_{th}(r_0)$ and $F_{th}^a(r_0)$ are the threshold of SWCNTs in terms of local (peak) fluence and average fluence, respectively. In this study, radius of disappearance, $r_0$, was experimentally determined by comparing AFM images of SWCNTs before and after ablation. The laser beam radius $w_0$ was characterized using a previously published method. To be consistent with most literature using average fluence as threshold fluence, $F_{th}^a(r_0)$ equivalent to half of $F_{th}(r_0)$ was employed.

FIGS. 19(a) and 19(b) show AFM images of SWCNTs on a glass substrate before and after irradiation with a single laser pulse at an average fluence of 2.8 $J/cm^2$. Using fluences slightly above the glass ablation threshold of 2.6 J/cm², debris due to ablation could be minimized and impairing the AFM imaging prevented. As shown in the cross-sectional profile in FIG. 19(c), most SWCNTs were bundled together with diameter of 5-25 nm (see also FIG. 18). The ablation of SWCNTs in a bundled state is of practical interest since bundled carbon nanotubes commonly exist in many applications, such as chemical sensors and electronic devices. There are about 30 SWCNT bundles per 10 µm² area, and the average bundle length is about 2 µm. The arrow in FIG. 19(b) indicates the direction of the laser polarization. The center of the laser beam is represented by the cross of two perpendicular lines. The corresponding Gaussian distribution of laser fluence is plotted in FIG. 19(d). Three concentric white circles are drawn to indicate three distinguished regions. The large circle (No. 1) indicates the region where 95% of carbon nanotubes were ablated, the medium circle (No. 2) indicates the region of glass ablation at the nanoscale, and the small circle (No. 3) indicates the region of direct femtosecond laser ablation of glass at the microscale. The radius $r_0$ of SWCNTs disappearance indicated by the large white circle is 5.35 µm, corresponding to an average threshold fluence of $F_{th}^a(r_0)=26$ mJ/cm² for SWCNTs' ablation.

FIG. 20 presents details of the glass ablation region presented within the medium and small circles shown in FIG. 19. A few elliptical and rectangular dotted shapes are added in the AFM images to highlight the regions of glass nanoablation before and after laser exposure. It was observed that the glass nanoablation seen in FIG. 20(b) took place at the same exact positions of carbon nanotubes in FIG. 20(a). These nanolines on glass have the similar orientation and length of the carbon nanotubes that previously occupied those locations. The cross-sectional profiles along A-B and A'-B' before and after ablation are plotted in FIG. 20(c) demonstrating clearly that the nanoablation occurs on glass directly beneath SWCNTs. The width of the nanoablated lines is between 30-50 nm and the depth is up to 50 nm. Direct femtosecond laser ablation of glass was also observed at the center of laser beam up to a radius of 1.1 µm, as shown by the small circle in FIG. 19. This radius corresponds to an average threshold fluence of 2.3 J/cm² which is close to the published threshold of glass ablation of 2.6 J/cm². The circular distribution of nanoablation region allows its threshold fluence to be estimated. The measured distance from the center of the laser beam was 3.6 µm, which corresponds to average fluence of 420 mJ/cm². This value is about 6 times lower than the expected threshold of glass ablation.

To estimate the ablation thresholds, additional experiments were performed for a variety of average laser fluences ranging from 1.74 J/cm² to 0.1 J/cm². At laser energies as low as 1.12 J/cm², direct femtosecond laser ablation of glass was not observed even though at this fluence the nanoablation of glass could still be obtained. We analyzed the laser-exposed regions using AFM and measured the radius of circles indicating the disappearance of carbon nanotubes, the border of the nanoablated regions on glass, and the border of the femtosecond laser ablation craters on glass. FIG. 21 presents the measured radius data as a function of the local average fluence. Linear fits to data points based on Equation 4 reveals the linear relationship between the squared radius, of the ablation crater and logarithm of laser fluence. The extrapolation of the linear fit to $r^2=0$ results in average threshold fluences for glass ablation, glass nanoablation, and ablation of SWCNTs of 2.05±0.1 J/cm², 460±38 mJ/cm², and 25±6 mJ/cm², respectively. The measured ablation threshold of bundled SWCNTs is about 10 times lower than the theoretically calculated value for the ablation of single SWCNTs (~250 mJ/cm²). The reason for this discrepancy might be due to the fact that the theoretical value for single SWCNT was computed based on the estimated data for graphite. The calculated threshold fluence for SWCNTs is indeed similar to that for graphite (130-250 mJ/cm²). On the other hand, it is also possible that these lower values of measured ablation thresholds are a result of a possible plasmonic enhancement between the bundled nanotubes.

Notably, the threshold fluence for glass nanoablation is approximately 4.5 times smaller than the measured threshold for fs-laser ablation of glass. We may attribute this nanoablation phenomenon to a possible local-field enhancement near the carbon nanotube bundles. We have previously showed that the near-field enhancement of fs-laser pulses can be used to overcome the diffraction limit of traditional laser ablation for patterning silicon at the nanoscale using gold nanoparticles. Enhancement of electromagnetic fields near the surface of nanoparticles is a result of the excitation of localized surface plasmons as well as the lightning rod effect in metallic nanostructures. Surface plasmons are collections of electrons that oscillate at the interface between the metal and its surrounding dielectric material.

A number of experimental studies detected surface plasmons in multi-wall carbon nanotubes (MWCNTs), bundles of SWCNTs, and purified SWCNTs using electron energy loss spectroscopy (EELS). These studies showed two main peaks identified as surface plasmons in the ranges of 5-7.5 eV and 21-27 eV. Careful EELS measurements by Pitchler et. al. showed some additional peaks at energies below 3.5 eV. Bose, later attributed these peaks to possible surface plasmons related to the collective azimuthal motion of electrons on the surface of the nanotubes. More recent experiments demonstrated the nanoantenna operation of MWCNTs as well as their photon coupling capacity (near 2.3 eV) using a fluorescent microbead detection.

Despite these studies providing some insight on the plasmonic features of carbon nanotubes, our present understanding of their collective electronic excitation modes or plasmons is still limited. Especially, considering the mixed metallic and semiconducting nature of SWCNT bundles, further studies are needed to elucidate the exact nature of the near-field enhancement phenomena observed in this study.

Conclusions

We studied the properties of fs-laser ablation of SWCNTs. We found that the average fluence threshold for ablation of SWCNTs in a bundle state is 25 mJ/cm². This value is 5-10 times smaller than the measured fs-laser ablation threshold for graphite and 10 times smaller than that calculated for the ablation of single nanotubes. At an average laser fluence of 460 mJ/cm², we observed nanoablation of glass directly beneath the bundled SWCNTs and creation of micrometers long nanolines. The nanoablations are believed to be due to near-field enhancement of the electric field near the bundled SWCNTs. This enhancement by carbon nanotubes could potentially be used in a number of applications. It could possibly be used for lithographic patterning on various materials for electronic as well as for biological applications. Recently, Chen et al. developed a new technique to interface biocompatible CNTs with a cell surface by carbohydrate-receptor interactions: the modified CNTs are nontoxic and bind to specific sites on cell surfaces. Through this method it might be possible to use the near-field enhancement of SWCNTs to kill cancer cells by irradiating SWCNT labeled cancer cells with ultrafast laser pulses. The advantage of the near-field enhancement is that it only damages atto-litter volumes around the SWCNTs. In addition to the nanoscale localization of laser pulses the nonthermal nature of fs-laser ablation can be exploited to minimize destruction of surrounding healthy cells.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

REFERENCES

The following references are all incorporated by reference to the extent they provide information available to one of ordinary skill in the art regarding the implementation of the technical teachings of the invention.

2. Mie, G., Beitrage zur Optik truber Medien, speziell kollaidaler Metallosungen. Annalen der Physik, 1908. 25(3): p. 337-445.
3. Yguerbide, J., et al., Light Scattering Submicroscopic Particles as Highly Fluorescent Analogs and Their Use as Tracer Labels in Clinical and Biological Applications: I. Theory. Analytical Biochemistry, 1998. 262: p. 137-156.
4. Yguerbide, J., et al., Light Scattering Submicroscopic Particles as Highly Fluorescent Analogs and Their Use as Tracer Labels in Clinical and Biological Applications: I. Experimental Characterization. Analytical Biochemistry, 1998. 262: p. 157-176.
5. Frens, G., Controlled nucleation for the regulation of the particle size in monodisperse gold suspensions. Nat. Phys. Sci., 1973. 241: p. 20-22.
6. Sokolov, K., Gold Nanoparticles as Molecular Specific Contrast Agents for Real Time Vital Optical Imaging. Cancer Research, 2003. 63: p. 1999-2004.
7. Downer, M. C., et al., Femtosecond imaging of melting anf evaporation at a photoexcited silicon surface. J. Opt. Soc. Am. B. 1985. 2(4): p. 595-599.
8. Borowiec, A., et al., Transmission and scanning electron microscopy studies of single femtosecond-laser-pulse ablation of silicon. Appl. Phys. A., 2003(76): p. 201-207.
9. Bonse, J., et al., Modifying single-crystalline silicon by femtosecond laser pulses: an analysis by micro Raman spectroscopy, scanning laser microscopy and atomic force microscope. Appl. Surf Sci., 2004(221): p. 215-230.
10. Ben-Yakar, A., Femtosecond laser ablation properties of borosilicate glass. Journal of Applied Physics, 2004. 98(9): p. 5316-5323.
11. Nolte, S., et al., Ablation of metals by ultrashort laser pulses. J. Opt. Soc. Am. B. 1997. 14(10): p. 2716-2722.
12. Ashkenasi, D., et al., Appl. Surf Sci., 1999. 150: p. 101.
13. McDonald, J. P., et al., Role of a native oxide on femtosecond laser interaction with silicon (100) near the damage threshold. Appl. Phys. Lett., 2005. 86: p. 86-86.
14. Downer, M. C., et al., Femtosecond imaging of melting and evaporation at a photoexcited silicon surface. J. Opt. Soc. Am. B. 1985. 2(4): p. 595-599.
15. Jhee, Y. K., et al., Charge emission and precursor accumulation in the multiple-pulse damage regime of silicon. J. Opt. Soc. Am. B. 1985. 2(10): p. 1626-1633.
16. Bonse, J., et al., Femtosecond laser ablation of silicon-modification thresholds and morphology. Appl. Phys. A, 2002. 74: p. 19-25.
17. Ben-Yakar, A., et al., Morphology of femtosecond-laser-ablated borosilicate glass surfaces. Applied Physics Letters, 2003. 83(15): p. 3030-3032.
18. Quinten, M., Local fields close to the surface of nanoparticles and aggregates of nanoparticles. Appl. Phys. B. 2001. 73: p. 245-255.
19. Rechberger, W., et al., Optical properties of two interacting gold nanoparticles. Opt Commun., 2003(220): p. 137-141.
20. Kreibig, U., et al., Optical Absorption of Small Metallic Particles. Surf Science, 1985. 156: p. 678-700.
21. Messinger, B. J., et al., Local fields at the surface of noble-metal microspheres. Phys. Rev. B. 1981. 24(2): p. 649-657.
22. Stuart, B. C., Nanosecond-to-Femtosecond Laser Induced Breakdown in Dielectrics. Phys. Rev. B. 1996. 53(4): p. 1749-1761.
23. Vogel, A., et al., Mechanisms of femtosecond laser nanosurgery of cells and tissues. Journal of Physics, 2005.
24. Loo, C., et al., Immunotargeted Nanoshells for Integrated Cancer Imaging and Therapy. Nano Letters, 2005. 5(4): p. 709-711.
25. Pitsillides, C. M., et al., Selective Cell Targeting with Light-Absorbing Microparticles and Nanoparticles. Biophysical Journal, 2003. 84: p. 4023-4032.
26. Huttmann, G., et al., On the Possibility of High-Precision Photothermal Microeffects and the Measurement of Fast Thermal Denaturation of Proteins. IEEE J. Quantum Electron., 1999. 5(4): p. 954-962.
27. A. A. Gorbunov, W. Pompe, Phys. Status Solid. A, 145, 333 (1994)
28. J. Jearsch, F. Demming, L. J. Hildenhagen, K. Dickmann, Appl. Phys. A, 66, 29 (1997)
29. K. Wilder, C. F. Quate, D. Adderton, R. Bernstein, V. Elings, Appl. Phys. Lett., 77, 2527 (1998)
30. A. Chimmalgi, C. P. Grigoropoulos, K. Komvopoulos, J. Appl. Phys., 97, 104319 (2005)
31. S, Nolte, B. N. Chichkov, H. Welling, Y. Shani, K. Lieberman, H. Terkel, Opt. Lett., 24, 914 (1999)
32. L. Wang, E. X. Jin, S. M. Uppuluri, X. Xu, Opt. Exp., 14, 9902 (2006)
33. D. J. Hwang, A. Chimmalgi, C. P. Grigoropoulos, J. Appl. Phys., 99, 044905 (2006)
34. W. Srituravanich, N. Fang, C. Sun, Q. Luo, X. Zhang, Nano Lett., 4, 1085 (2004)
35. S. M. Huang, M. H. Hong, B. Luk'yanchuk, T. C. Chong, Appl. Phys. A, 77, 293 (2003)
36. W. Cai, R. Piestun, Appl. Phys. Lett. 88, 111112 (2006)
37. S. M. Huang, M. H. Hong, B. Luk'yanchuk, T. C. Chong, Appl. Phys. Lett., 82, 4809 (2003)
38. N. N. Nedyalkov, H. Takada, M. Obara, Appl. Phys. A, 85, 163 (2006)
39. N. N. Nedyalkov, T. Sakai, T. Miyanishi, M. Obara, J. Phys. D: Appl. Phys., 39, 5037 (2006)
40. P. Leiderer, C. Bartels, J. Konig-Birk, M. Mosbacher, J. Boneberg, Appl. Phys. Lett., 85, 5370 (2004)
41. M. F. Yanik, H. Cinar, H. N. Cinar, A. D. Chisholm, Y. Jin, A. Ben-Yakar, Nature, 432, 822 (2004)
42. U. K. Tirlapur, K. Konig, Nature, 418, 290 (2002)
43. N Shen, D. Datta, C. B. Schaffer, P. LeDuc, D. E. Ingber, E. Mazur, Mech. Chem. Biosyst., 2, 17 (2005)
44. A. Vogel, J. Noack, G. Huttman, G. Paltauf, Appl. Phys. B. 81, 1015 (2005)

45. H. Hovel, S. Fritz, A. Hilger, U. Kreibig, M. Vollmer, Phys. Rev. B. 48, 178 (1993)
46. S. Nolte, B. N. Chichkov, H. Welling, Y. Shani, K. Lieberman, H. Terkel, Opt. Lett., 24, 914 (1999)
47. J. M. Liu, Opt Lett., 7, 196 (1982)
48. A. Ben-Yakar, R. L. Byer, J. of Appl. Phys., 98, 5316 (2004)
49. B. J. Messinger, K. Ulrich von Raben, R. K. Chang, P. W. Barber, Phys. Rev. B. 24, 649 (1981)
50. M. Quinten, Appl. Phys. B. 73, 245 (2001)
51. S. Nolte, C. Momma, H. Jacobs, A. Tunnermann, B. N. Chichkov, B. Wellegehausen, H. Welling, J. Opt. Soc. Am. B. 14, 2716 (1997)
52. S. K. Sundaram, E. Mazur, Nat. Mat., 1, 217 (2002)
53. J. Bonse, S. Baudach, J. Kruger, W. Kautek, M. Lenzer, Appl. Phys. A, 74, 19 (2002)
54. A. Plech, V. Kotaidis, M. Lorenc, J. Boneberg, Nat. Phys., 2, 44 (2006)
55. B. S. Luk'yanchuk, Z. B. Wang, W. D. Song, M. H. Hong, Appl. Phys. A 79, 747 (2004)
56. G. R. Jellison Jr., D. H. Lowndes, Appl. Phys. Lett., 51, 352 (1987)
57. Ben-Yakar, A.; Byer, R. L. Journal of Applied Physics 2004, 96, (9), 5316-5323.
58. Loesel, F. H.; Fischer, J. P.; Gotz, M. H.; Horvath, C.; Juhasz, T.; Noack, F.; Suhm, N.; Bille, J. F. Applied Physics B-Lasers and Optics 1998, 66, (1), 121-128.
59. Choi, T. Y.; Grigoropoulos, C. P. Journal of Applied Physics 2002, 92, (9), 4918-4925.
60. Perry, M. D.; Stuart, B. C.; Banks, P. S.; Feit, M. D.; Yanovsky, V.; Rubenchik, A. M. Journal of Applied Physics 1999, 85, (9), 6803-6810.
61. Vogel, A.; Noack, J.; Huttman, G.; Paltauf, G. Applied Physics B-Lasers and Optics 2005, 81, (8), 1015-1047.
62. Keren, K.; Berman, R. S.; Buchstab, E.; Sivan, U.; Braun, E. Science 2003, 302, (5649), 1380-1382.
63. Gao, H. J.; Kong, Y.; Cui, D. X.; Ozkan, C. S, Nano Letters 2003, 3, (4), 471-473.
64. Besteman, K.; Lee, J. O.; Wiertz, F. G. M.; Heering, H. A.; Dekker, C. Nano Letters 2003, 3, (6), 727-730.
65. Panchapakesan, B. L., S.; Sivakumar, K.; Teker, K.; Cesarone, G.; and Wickstrom, E. NanoBiotechnology 2005, 1, 133-139.
66. Liu, Z.; Cai, W. B.; He, L. N.; Nakayama, N.; Chen, K.; Sun, X. M.; Chen, X. Y.; Dai, H. J. Nature Nanotechnology 2007, 2, (1), 47-52.
67. Link, S.; El-Sayed, M. A. Journal of Physical Chemistry B 1999, 103, (40), 8410-8426.
68. Oldenburg, S. J.; Averitt, R. D.; Westcott, S. L.; Halas, N. J. Chemical Physics Letters 1998, 288, (2-4), 243-247.
69. Huang, X. H.; El-Sayed, I. H.; Qian, W.; El-Sayed, M. A. Journal of the American Chemical Society 2006, 128, (6), 2115-2120.
70. Loo, C.; Lowery, A.; Halas, N.; West, J.; Drezek, R. Nano Letters 2005, 5, (4), 709-711.
71. El-Sayed, I. H.; Huang, X. H.; El-Sayed, M. A. Cancer Letters 2006, 239, (1), 129-135.
72. Eversole, D.; Luk'yanchuk., B.; Ben-Yakar, A. Applied Physics A: Material Science and Processing 2007, In Press.
73. Reitze, D. H.; Wang, X.; Ahn, H.; Downer, M. C. Physical Review B 1989, 40, (17), 11986-11989.
74. Preuss, S.; Stuke, M. Applied Physics Letters 1995, 67, (3), 338-340.
75. Lenner, M.; Kaplan, A.; Palmer, R. E. Applied Physics Letters 2007, 90, (15).
76. Jeschke, H. O.; Garcia, M. E. Applied Surface Science 2002, 197, 107-113.
77. Jeschke, H. O.; Garcia, M. E.; Bennemann, K. H. Physical Review Letters 2001, 8701, (1).
78. Corio, P.; Santos, P. S.; Pimenta, M. A.; Dresselhaus, M. S. Chemical Physics Letters 2002, 360, (5-6), 557-564.
79. Ma, R. Z.; Wei, B. Q.; Xu, C. L.; Liang, J.; Wu, D. H. Carbon 2000, 38, (4), 636-638.
80. Romero, A. H.; Garcia, M. E.; Valencia, F.; Terrones, H.; Terrones, M.; Jeschke, H. O, Nano Letters 2005, 5, (7), 1361-1365.
81. Kocabas, C.; Meitl, M. A.; Gaur, A.; Shim, M.; Rogers, J. A. Nano Letters 2004, 4, (12), 2421-2426.
82. Liu, J.; Rinzler, A. G.; Dai, H. J.; Hafner, J. H.; Bradley, R. K.; Boul, P. J.; Lu, A.; Iverson, T.; Shelimov, K.; Huffman, C. B.; Rodriguez-Macias, F.; Shon, Y. S.; Lee, T. R.; Colbert, D. T.; Smalley, R. E. Science 1998, 280, (5367), 1253-1256.
83. Chen, J.; Hamon, M. A.; Hu, H.; Chen, Y. S.; Rao, A. M.; Eklund, P. C.; Haddon, R. C. Science 1998, 282, (5386), 95-98.
84. Sabba, Y.; Thomas, E. L. Macromolecules 2004, 37, (17), 6662-6662.
85. Saran, N.; Parikh, K.; Suh, D. S.; Munoz, E.; Kolla, H.; Manohar, S. K. Journal of the American Chemical Society 2004, 126, (14), 4462-4463.
86. Krupke, R.; Hennrich, F.; Weber, H. B.; Beckmann, D.; Hampe, O.; Malik, S.; Kappes, M. M.; Lohneysen, H. V. Applied Physics a—Materials Science & Processing 2003, 76, (3), 397-400.
87. Kamat, P. V.; Thomas, K. G.; Barazzouk, S.; Girishkumar, G.; Vinodgopal, K.; Meisel, D. Journal of the American Chemical Society 2004, 126, (34), 10757-10762.
88. Dumitrica, T.; Garcia, M. E.; Jeschke, H. O.; Yakobson, B. I. Physical Review B 2006, 74, (19), 193406-193409.
89. Sokolowski-Tinten, K. K., S.; Temnov, V.; Biakowski, J.; Vonder Linde, D.; Cavalleri, A.; Jeschke, H. O.; Garcia, M. E.; Bennemann, K. H., Ultrafast phenomena XII. Springer Series in Chemical Physics: 2000; Vol. 66, p 425.
90. Barnes, W. L.; Dereux, A.; Ebbesen, T. W. Nature 2003, 424, (6950), 824-830.
91. Pichler, T.; Knupfer, M.; Golden, M. S.; Fink, J.; Rinzler, A.; Smalley, R. E. Physical Review Letters 1998, 80, (21), 4729-4732.
92. Bose, S. M. Physics Letters A 2001, 289, (4-5), 255-256.
93. Chen, X.; Tam, U. C.; Czlapinski, J. L.; Lee, G. S.; Rabuka, D.; Zettl, A.; Bertozzi, C. R. Journal of the American Chemical Society 2006, 128, (19), 6292-6293.

What is claimed is:

1. A method comprising:
   positioning a nanoparticle in proximity to a surface of a material;
   irradiating the nanoparticle with a laser tuned to the nanoparticle's plasmonic frequency; and
   allowing a near-field effect from the irradiated nanoparticle to photodamage the material.

2. The method of claim 1, wherein the nanoparticle comprises one or more noble metals.

3. The method of claim 1, wherein the nanoparticle has a spherical or an anisotropic shape.

4. The method of claim 1, wherein the nanoparticle comprises a carbon structure.

5. The method of claim 1, wherein the nanoparticle is a single wall carbon nanotube.

6. The method of claim 1, wherein the nanoparticle is irradiated with one or more laser pulses chosen from femtosecond, picosecond, and nanosecond pulses.

7. The method of claim 1, wherein the nanoparticle is conjugated to at least one subcellular location.

8. The method of claim 1, wherein the nanoparticle is conjugated to at least one subcellular location chosen from an antibody-mediated receptor, a peptide mediated receptor, a subcellular organelle, a DNA base pair, and an RNA base pair.

9. The method of claim 1, wherein the material is a biological material.

10. The method of claim 1, wherein the material is one or more biological materials chosen from a bone, cell, subcellular site, extracellular site, atherosclerotic plaque, blood clot, connective tissue, tumor, and cellular targeting region.

11. The method of claim 1, wherein the material comprises one or more solids chosen from a silicon, glass, polymer, plastic, graphite, ceramic, metal, and Hafnium.

12. The method of claim 1, wherein the step of positioning the nanoparticle in proximity to the surface of the material comprises attaching the nanoparticle to the surface of the material.

13. A method comprising:
    positioning a nanoparticle in proximity to a surface of a material;
    irradiating the nanoparticle with a low peak power laser pulse;
    obtaining an image of the material;
    irradiating the nanoparticle with a laser tuned to the nanoparticle's plasmonic frequency; and
    allowing a near-field effect from the irradiated nanoparticle to photodamage the material.

14. The method of claim 10 wherein the step of irradiating the nanoparticle with a low peak power laser pulse does not substantially ablate the material.

15. The method of claim 10 wherein the step of irradiating the nanoparticle with a laser tuned to the nanoparticle's plasmonic frequency comprises emitting one or more laser pulses chosen from femtosecond, picosecond, and nanosecond pulses.

16. The method of claim 10, wherein the nanoparticle comprises one or more noble metals.

17. The method of claim 10, wherein the nanoparticle is conjugated to at least one subcellular location chosen from an antibody-mediated receptor, a peptide mediated receptor, a subcellular organelle, a DNA base pair, and an RNA base pair.

18. The method of claim 10, wherein the material is a biological material.

19. The method of claim 10, wherein the material comprises one or more solids chosen from a silicon, glass, polymer, plastic, graphite, ceramic, metal, and Hafnium.

20. The method of claim 10, wherein the material is one or more biological materials chosen from a bone, cell, subcellular site, extracellular site, atherosclerotic plaque, blood clot, connective tissue, tumor, and cellular targeting region.

* * * * *